(12) United States Patent
Kim et al.

(10) Patent No.: US 8,597,802 B2
(45) Date of Patent: Dec. 3, 2013

(54) ACRIDINE DERIVATIVE AND ORGANIC ELECTROLUMINESCENCE DEVICE INCLUDING THE SAME

(75) Inventors: Tae-Hyung Kim, Yongin-si (KR); Kyoung-Soo Kim, Yuseong-gu (KR)

(73) Assignee: Doosan Corporation, Seoul (KR)

( * ) Notice: Subject to any disclaimer, the term of this patent is extended or adjusted under 35 U.S.C. 154(b) by 22 days.

(21) Appl. No.: 13/378,851

(22) PCT Filed: Jun. 1, 2010

(86) PCT No.: PCT/KR2010/003526
§ 371 (c)(1),
(2), (4) Date: Mar. 7, 2012

(87) PCT Pub. No.: WO2010/147319
PCT Pub. Date: Dec. 23, 2010

(65) Prior Publication Data
US 2012/0168730 A1    Jul. 5, 2012

(30) Foreign Application Priority Data

Jun. 19, 2009 (KR) .................. 10-2009-0054895

(51) Int. Cl.
*H01L 51/54* (2006.01)
(52) U.S. Cl.
USPC ........... 428/690; 428/917; 313/504; 313/505; 313/506; 257/40; 257/E51.05; 257/E51.026; 257/E51.032; 546/18; 546/79; 546/81; 546/101

(58) Field of Classification Search
USPC ................. 428/690, 917; 313/504, 505, 506; 257/40, E51.05, E51.026, E51.032; 546/18, 79, 81, 101
See application file for complete search history.

(56) References Cited

FOREIGN PATENT DOCUMENTS

| DE | 10 2005 043 163 | * | 1/2006 |
|---|---|---|---|
| KR | 10-2005-0091080 A | | 9/2005 |
| KR | 1020050088993 | * | 9/2005 |
| KR | 10-2006-0051622 A | | 5/2006 |
| KR | 10-2007-0073011 A | | 7/2007 |
| WO | WO 2009/047147 A | | 4/2009 |

OTHER PUBLICATIONS

International Search Report cited in PCT/KR2010/003526, dated Feb. 21, 2011.

* cited by examiner

*Primary Examiner* — Gregory Clark
(74) *Attorney, Agent, or Firm* — Sughrue Mion, PLLC

(57) ABSTRACT

Disclosed are an acridine derivative and an organic electroluminescence device including the same. Specifically, the disclosed acridine derivative compound has an aryl moiety or a heteroaryl moiety, linked to an acridine moiety and an amine moiety, and the disclosed organic electro-luminescence device including the acridine derivative compound requires a low operating voltage, shows high efficiency, and is enhanced in life-span.

7 Claims, No Drawings

ACRIDINE DERIVATIVE AND ORGANIC ELECTROLUMINESCENCE DEVICE INCLUDING THE SAME

CROSS REFERENCE TO RELATED APPLICATIONS

This application is a National Stage of International Application No. PCT/KR2010/003526 filed Jun. 1, 2010, claiming priority based on Korean Patent Application No. 10-2009-0054895 filed Jun. 19, 2009, the contents of all of which are incorporated herein by reference in their entirety.

TECHNICAL FIELD

The present invention relates to an acridine derivative and an organic electro-luminescence device including the same. More particularly, the present invention relates to an acridine derivative compound having an aryl moiety or a heteroaryl moiety, linked to an acridine moiety and an amine moiety, and an organic electro-luminescence device including the acridine derivative compound, in which the organic electro-luminescence device requires a low operating voltage, shows high efficiency, and is enhanced in life span.

BACKGROUND ART

In general, an organic light emitting phenomenon indicates conversion of electric energy into light energy by means of an organic material. An organic electro-luminescence device using the organic light emitting phenomenon generally has a structure including a cathode, an anode, and an organic material layer interposed therebetween. Herein, in many cases, the organic material layer may have a multi-layered structure having respective different materials in order to improve efficiency and stability of an organic light emitting device. For example, it may include a hole injection layer, a hole transport layer, a light emitting layer, an electron transport layer, an electron injection layer, and the like.

In the structure of such an organic electro-luminescence device, when a voltage is applied between the two electrodes, holes from the anode and electrons from the cathode are injected into the organic material layer. When the injected holes combine with the injected electrons, excitons are formed. Then, when the excitons return to a ground state, light is generated.

Materials used as an organic material layer in an organic electro-luminescence device may be classified into a light emitting material, a hole injection material, a hole transport material, an electron transport material, an electron injection material, etc. according to their functions.

Further, the light emitting material can be classified into a blue, green or red light emitting material and a yellow or orange light emitting material required for giving a more natural color, according to a light emitting color. Also, a host/dopant system can be used as the light emitting material for the purpose of enhancing the color purity and the light emitting efficiency through energy transfer. It is based on the principle that if a small amount of a dopant having a smaller energy band gap and a higher light emitting efficiency than a host mainly forming a light emitting layer is mixed with the light emitting layer, excitons which are generated in the host are transported to the dopant, thus emitting a light having a high efficiency. Herein, since the wavelength of the host is moved according to the wavelength of the dopant, a light having a desired wavelength can be obtained according to the kind of the dopant.

Also, it was reported that as an electron transport material, organic metal complexes from among organic monomolecular materials, which have a high stability against electrons and show a relatively high electron moving speed, are preferable. Especially, Alq3 having a high stability and a high electron affinity was reported to be the most excellent, and is most basically used at present. Also, there are conventionally known electron transport materials such as a flavon derivative (Sanyo), or germanium and silicon cyclopentadiene derivatives (Chisso) (Japanese Patent Publication Nos. 1998-017860, and 1999-087067).

Also, as electron injection/transport materials, organic monomolecular materials having an imidazole group, an oxazole group, and a thiazole group have conventionally frequently been reported. However, before these materials were reported as the electron transport materials, the application of the materials' metal complex compounds to a blue light emitting layer or a blue-green light emitting layer of an organic electro-luminescence device had been already reported.

In order to allow the organic electro-luminescence device to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electro-luminescence device has not yet been fully realized. Accordingly, the development of new materials is continuously desired.

DISCLOSURE

Technical Problem

The present invention provides a novel organic compound capable of being applied to an organic electro-luminescence device, which is enhanced in color purity, luminous efficiency, luminance, power efficiency, and heat resistance.

Also, the present invention provides an organic electro-luminescence device including the novel organic compound, which requires a low operating voltage, shows a high efficiency, and is enhanced in life span.

Technical Solution

In accordance with an aspect of the present invention, there is provided a novel organic compound represented by Formula 1 below.

[Formula 1]

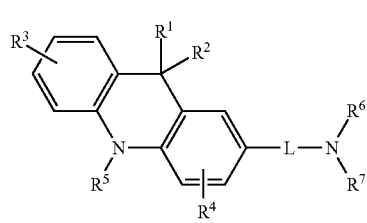

wherein, $R^1$ to $R^4$ are the same or different, and are selected from the group consisting of hydrogen, deuterium, halogen, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, a fused or non-fused $C_5$-$C_{60}$ heteroaryl group, a straight-chain or branched $C_1$-$C_{40}$ alkyloxy group, a fused or non-fused $C_6$-$C_{60}$ aryloxy group, and a fused or non-fused $C_6$-$C_{60}$ arylamine group;

$R^5$ to $R^7$ are the same or different, and are selected from the group consisting of hydrogen, deuterium, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, and a fused or non-fused $C_5$-$C_{60}$ heteroaryl group, and may form or not form a ring fused to an adjacent group;

L represents a $C_6$-$C_{60}$ arylene group or a $C_5$-$C_{60}$ heteroarylene group.

According to another aspect of the present invention, there is provided an organic electro-luminescence device including an (i) anode, (ii) a cathode, and (iii) one or more organic material layers intervened between the anode and the cathode, wherein at least one layer of the organic material layers includes the compound represented by Formula 1 according to the present invention.

Preferably, in the inventive organic electro-luminescence device, the organic material layer including the compound represented by Formula 1 may be at least one selected from the group including a hole injection layer, a hole transport layer and a light emitting layer.

Advantageous Effects

The inventive compound represented by Formula 1 is excellent in luminance, power efficiency, heat resistance, hole transport performance, and hole injection performance, and can show improvement in color purity and luminous efficiency. Thus, the compound may be used in at least one of a hole injection layer, a hole transport layer, and a light emitting layer in an organic electro-luminescence device. Accordingly, the inventive organic electro-luminescence device including the compound represented by Formula 1 requires a low operating voltage and shows a high efficiency, and thus is highly effective in performance maximization and life span improvement in a full-color organic EL panel.

BEST MODE

Mode for Invention

Hereinafter, exemplary embodiments of the present invention will be described with reference to the accompanying drawings.

The inventive compound represented by Formula 1 is an acridine derivative having an aryl moiety or a heteroaryl moiety, linked to an acridine moiety and an amine moiety. Also, the inventive compound represented by Formula 1 is any one material of a hole injection material, a hole transport material, a light emitting material, an electron transport material, and an electron injection material, and may be employed in an organic electro-luminescence device. Preferably, the compound is any one material of a hole injection material, a hole transport material, and a light emitting material, and may be employed in an organic electro-luminescence device.

In the inventive compound represented by Formula 1, $R^1$ to $R^4$ are the same or different, and are selected from the group consisting of hydrogen, deuterium, halogen, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, a fused or non-fused $C_5$-$C_{60}$ heteroaryl group, a straight-chain or branched $C_1$-$C_{40}$ alkyloxy group, a fused or non-fused $C_6$-$C_{60}$ aryloxy group, and a fused or non-fused $C_6$-$C_{60}$ arylamine group, and may form or not form a ring fused to an adjacent group.

Also, in Formula 1, $R^5$ to $R^7$ are the same or different, and are selected from the group consisting of hydrogen, deuterium, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, and a fused or non-fused $C_5$-$C_{60}$ heteroaryl group, and may form or not form a ring fused to an adjacent group.

Also, in Formula 1, L represents a $C_6$-$C_{60}$ arylene group, or a $C_5$-$C_{60}$ heteroarylene group. Non-limiting examples of L may include a $C_6$-$C_{60}$ arylene group or a $C_5$-$C_{60}$ heteroarylene group, selected from the group including phenylene, biphenylene, terphenylene, naphthylene, anthracenylene, phenanthrylene, pyrenylene, fluorenylene, fluoranthenylene, perylenylene, carbazolylene, N-carbazolephenylene, pyridinylene, quinolinylene and isoquinolinylene.

Also, in Formula 1, $R^1$ to $R^7$ and L each may be independently substituted or unsubstituted with at least one substituent selected from the group including deuterium, halogen, a nitrile group, a nitro group, a $C_1$-$C_{40}$ alkyl group, a $C_3$-$C_{40}$ cycloalkyl group, a $C_3$-$C_{40}$ heterocycloalkyl group, a $C_6$-$C_{60}$ aryl group, a $C_5$-$C_{60}$ heteroaryl group, a $C_1$-$C_{40}$ alkyloxy group, a $C_6$-$C_{60}$ aryloxy group and a $C_6$-$C_{60}$ arylamine group.

Examples of the compound represented by Formula 1 of the present invention include the following compounds, but the compound represented by Formula 1 of the present invention is not limited thereto.

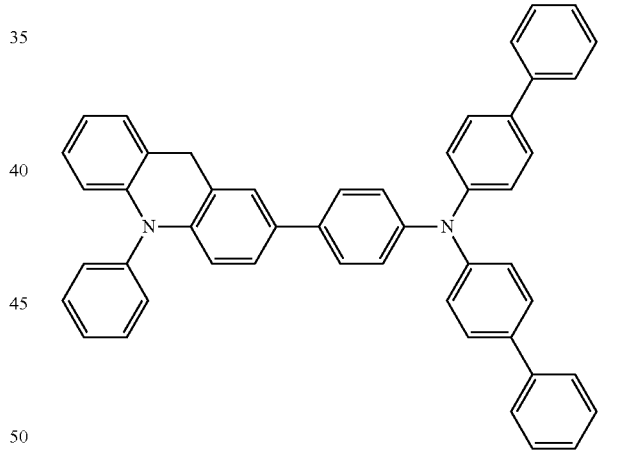

Cpd 1

Cpd 2
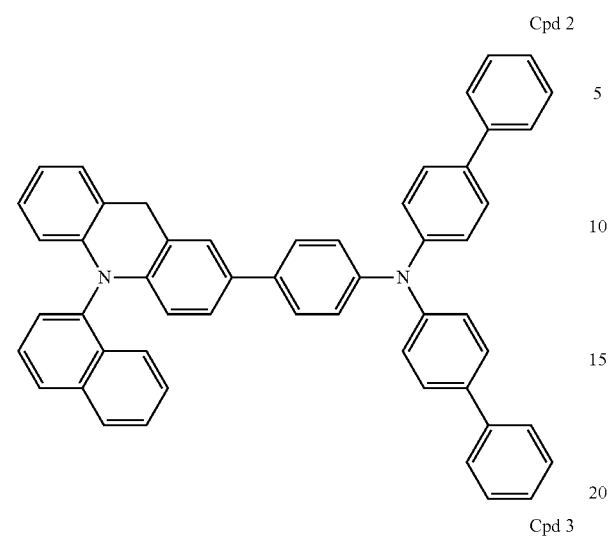
Cpd 5
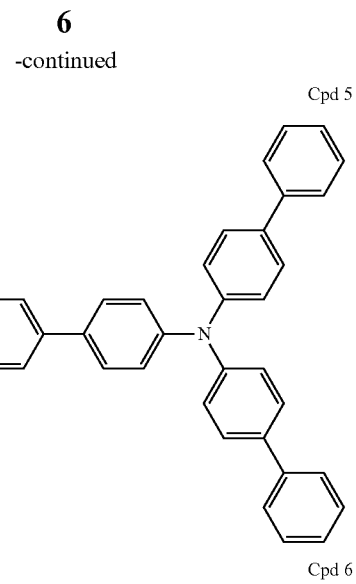
Cpd 3
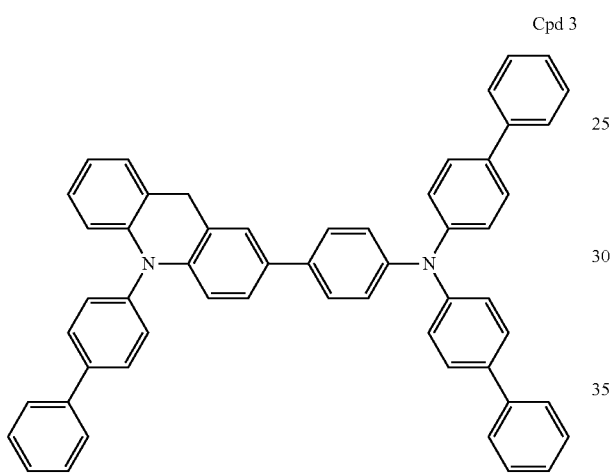
Cpd 6
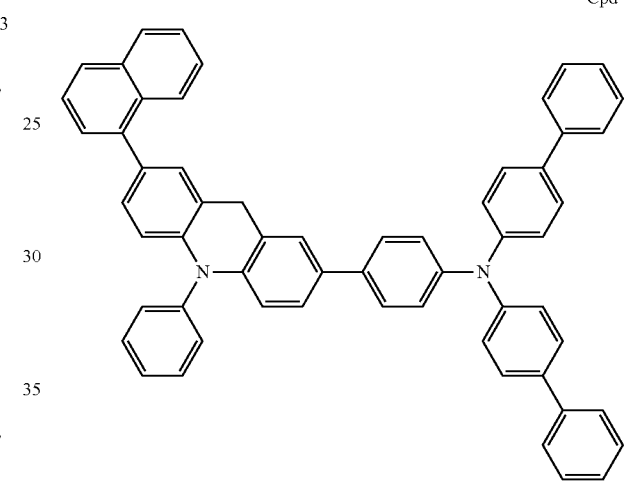
Cpd 4
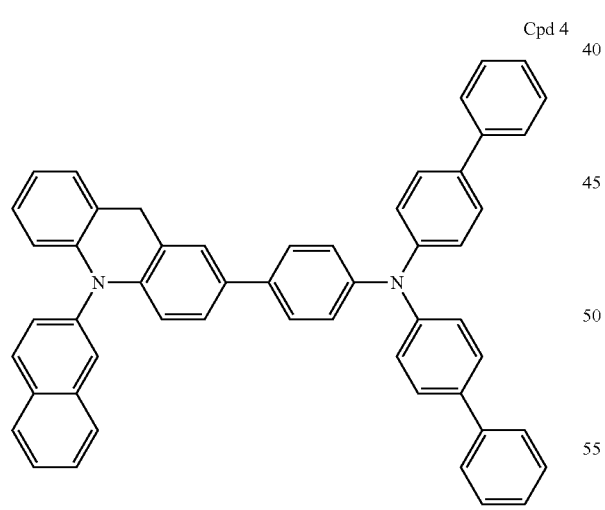
Cpd 7

Cpd 8
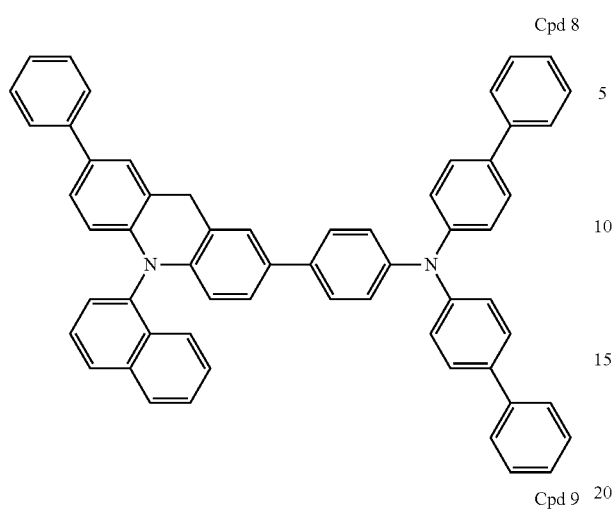
Cpd 11
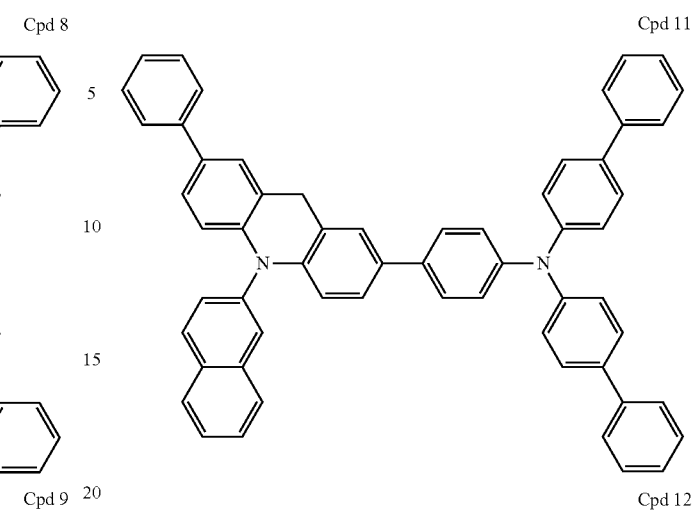
Cpd 9
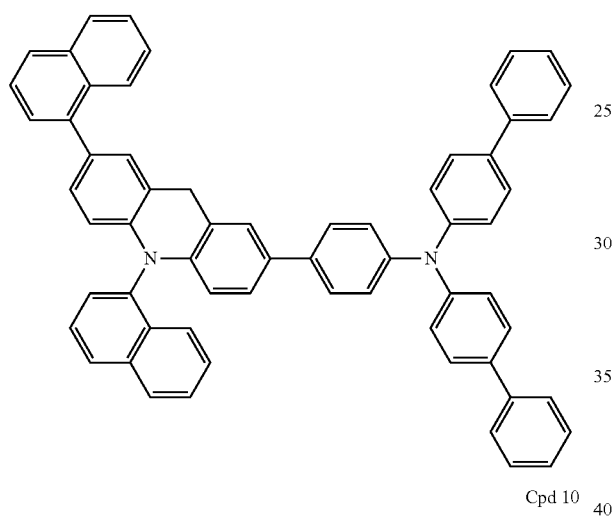
Cpd 12
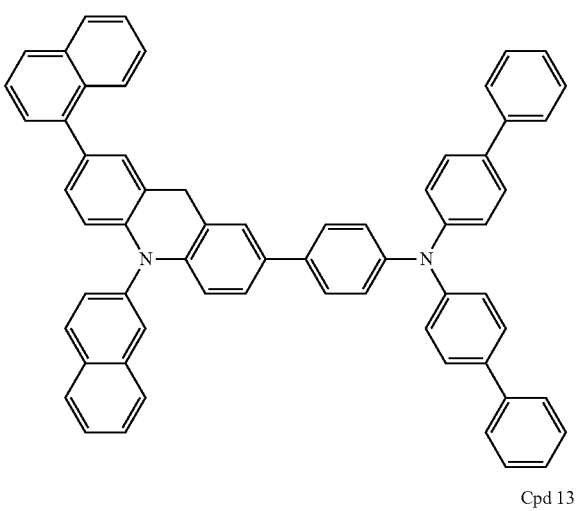
Cpd 10
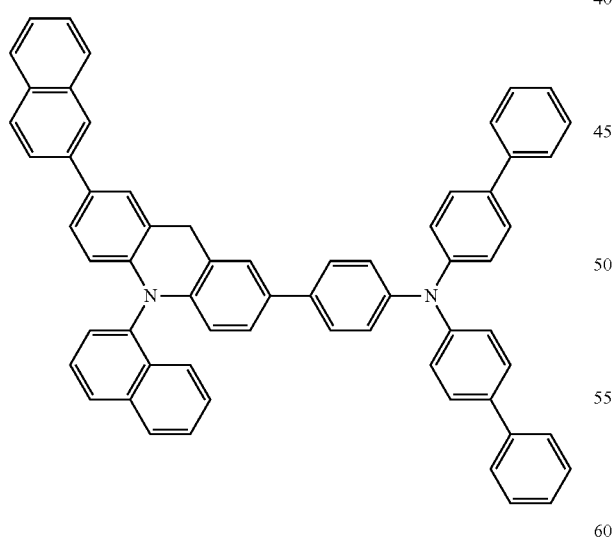
Cpd 13
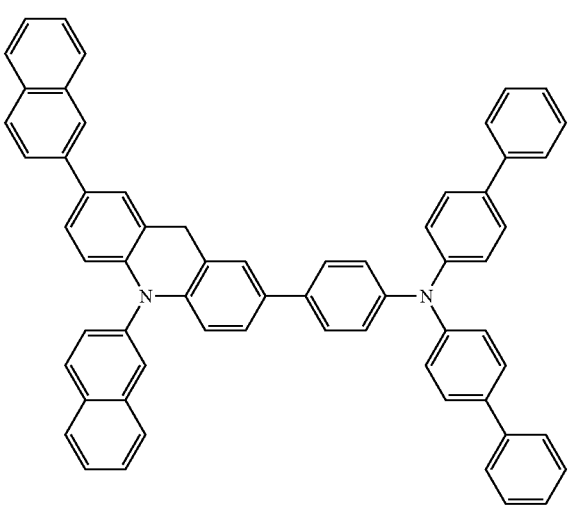

Cpd 14
Cpd 15
Cpd 16
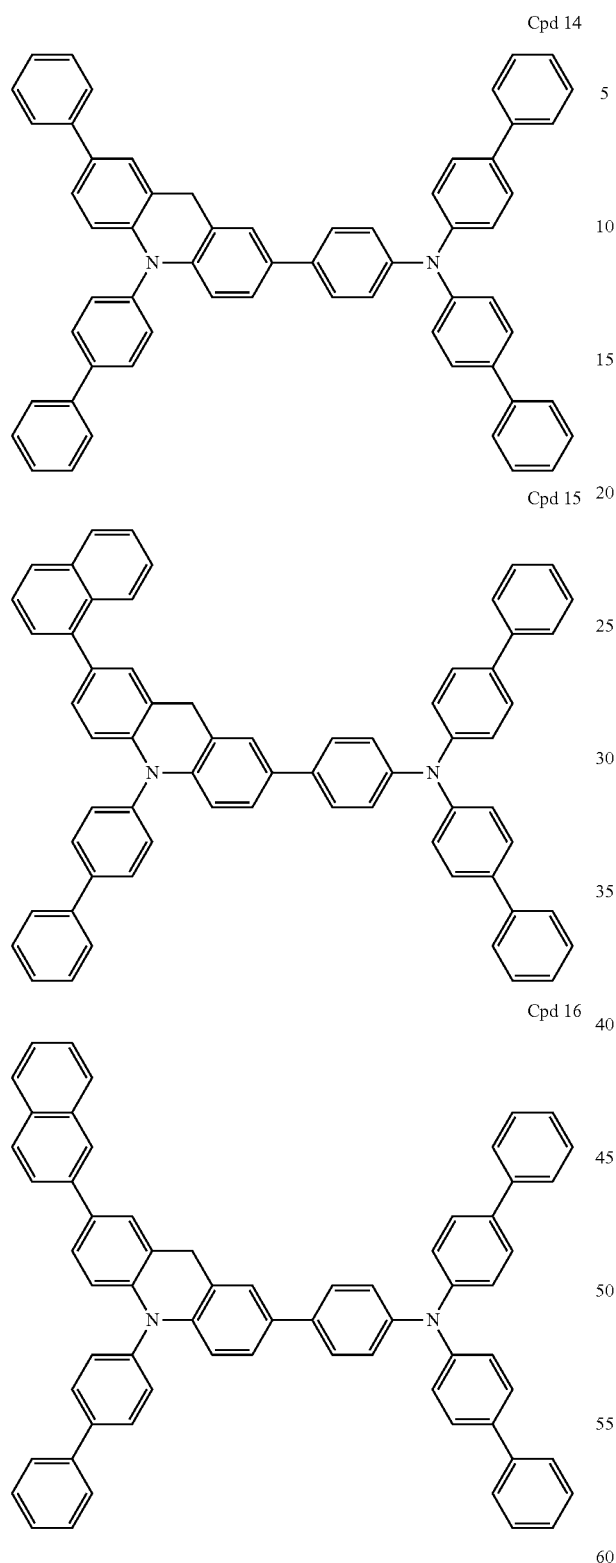
Cpd 17
Cpd 18
Cpd 19
Cpd 20
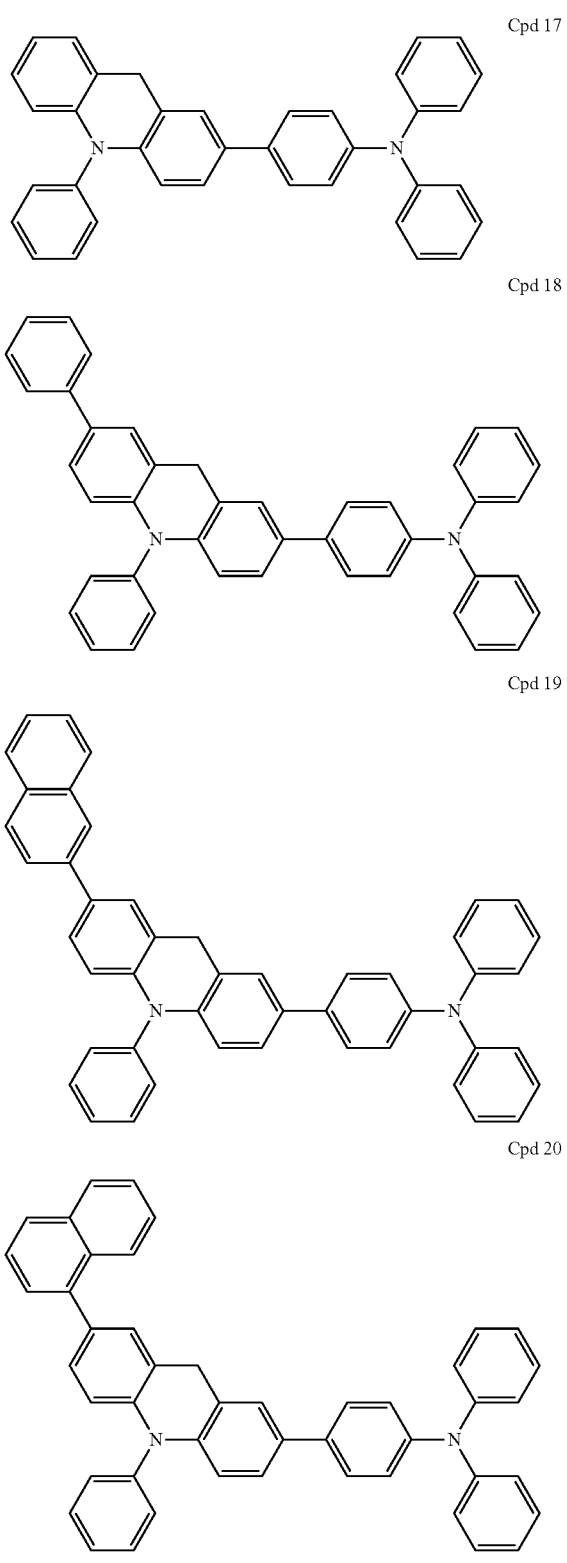

Cpd 21
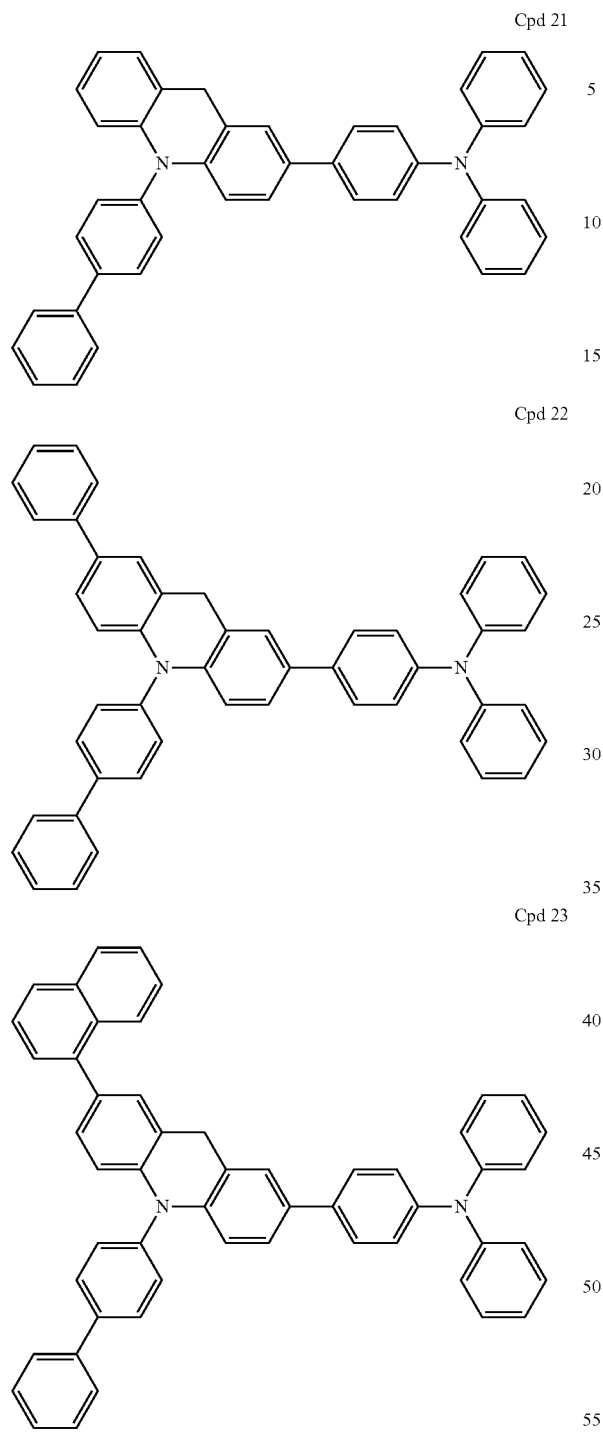
Cpd 22
Cpd 23
Cpd 24
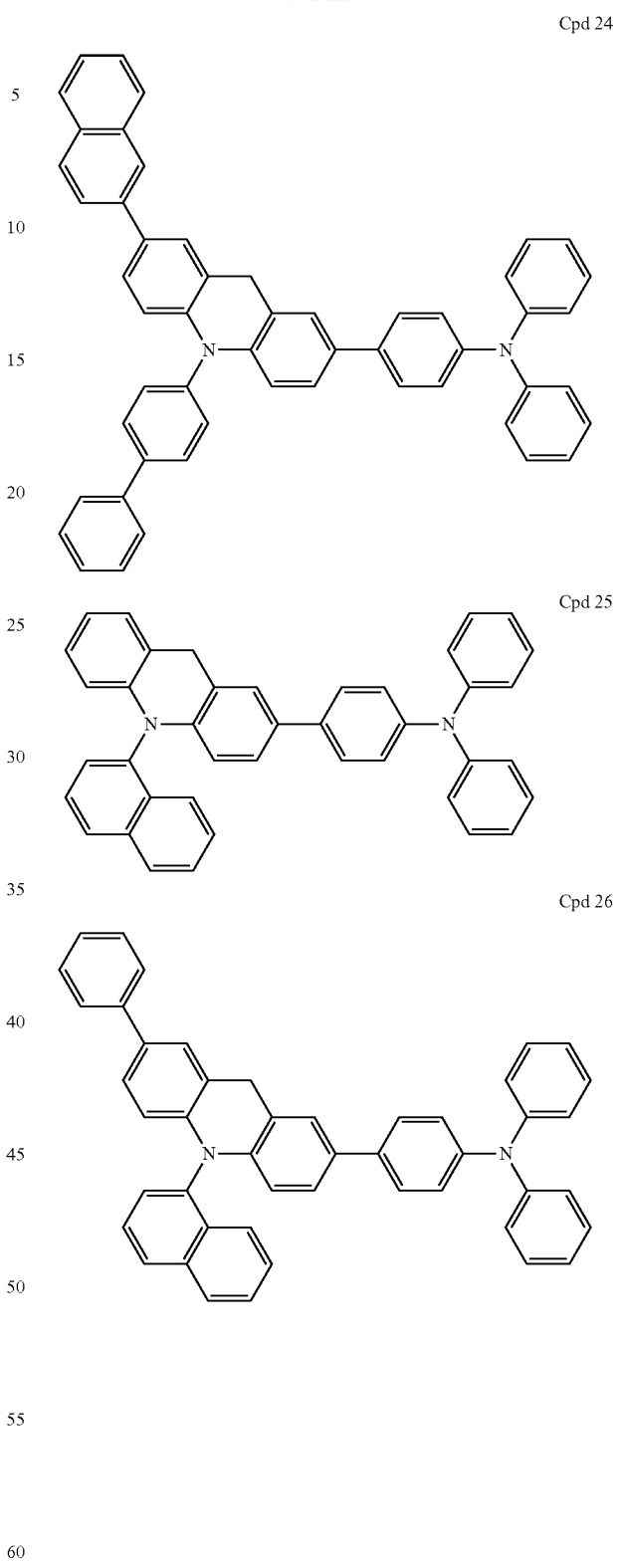
Cpd 25
Cpd 26

Cpd 27
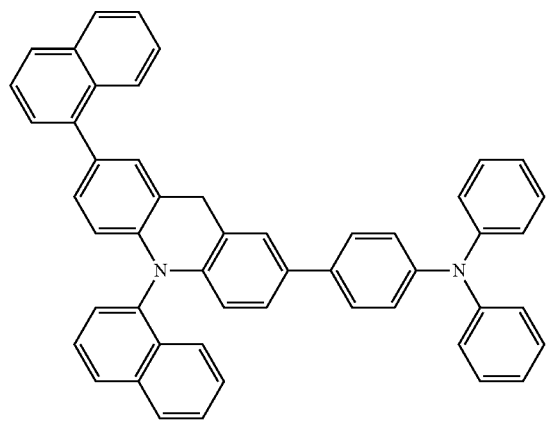
Cpd 28
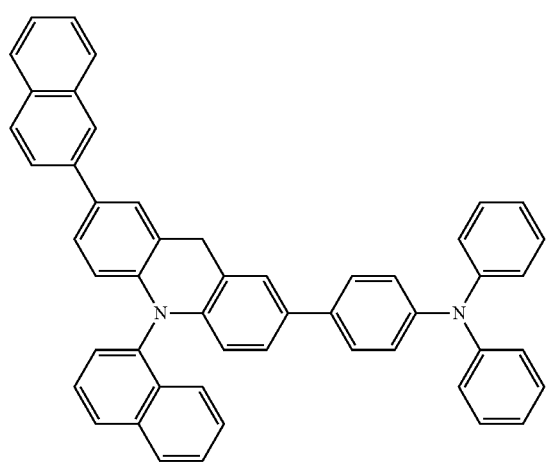
Cpd 29
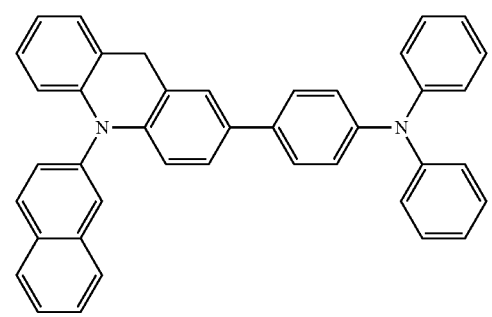
Cpd 30
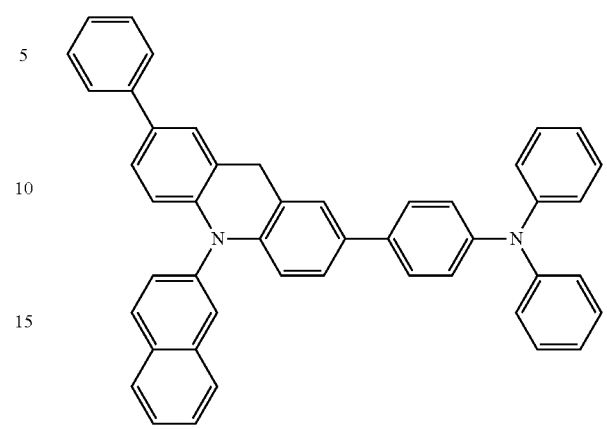
Cpd 31
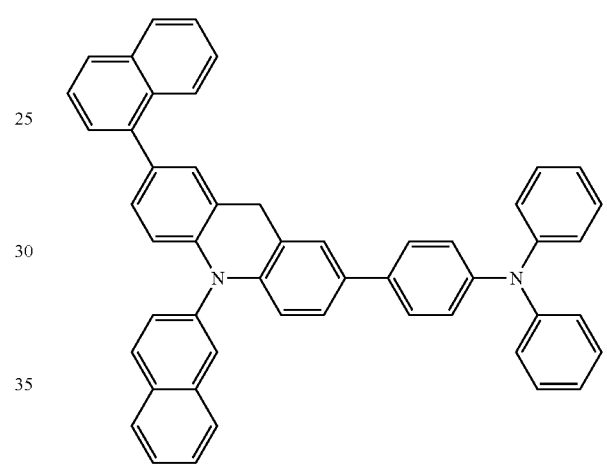
Cpd 32
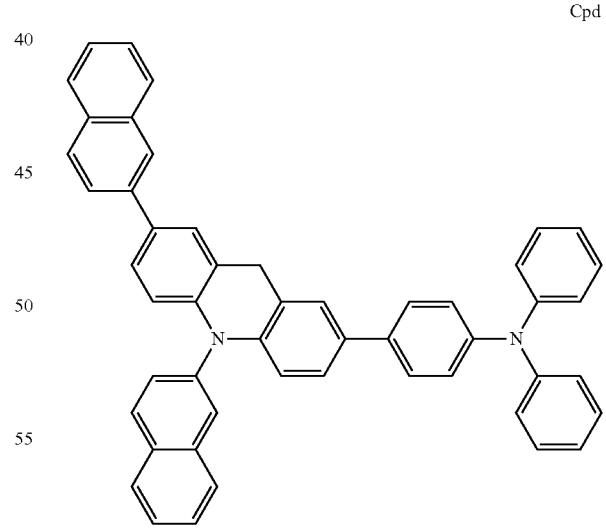

Cpd 33
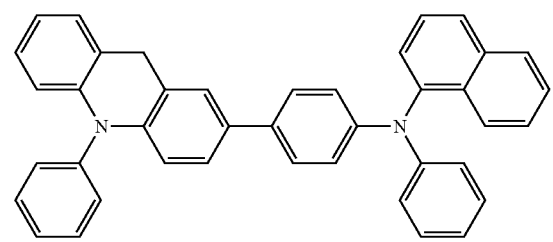
Cpd 34
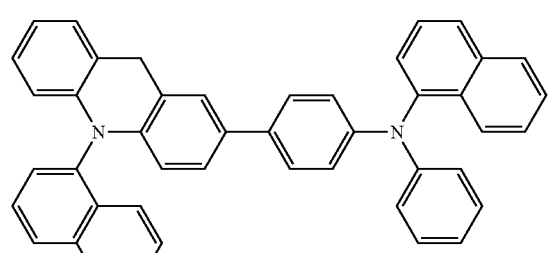
Cpd 35
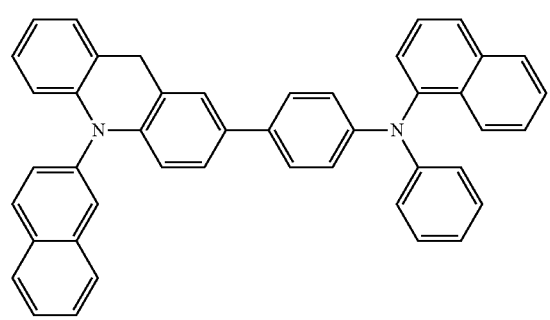
Cpd 36
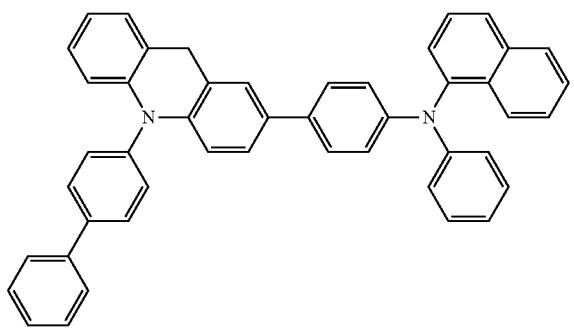
Cpd 37
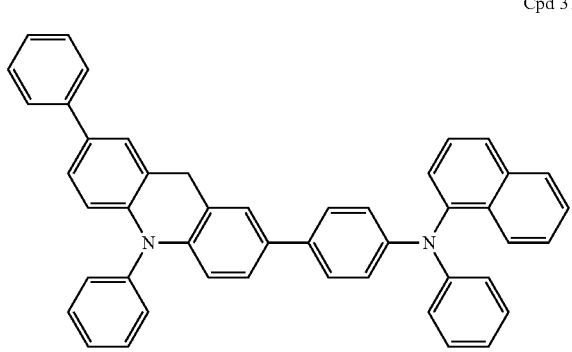
Cpd 38
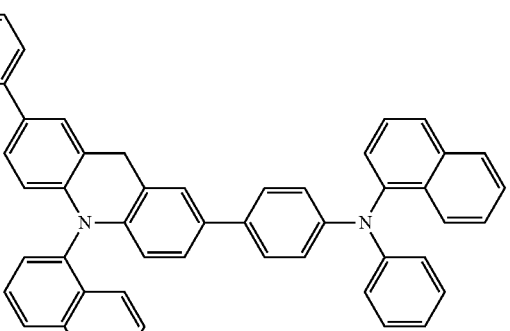
Cpd 39
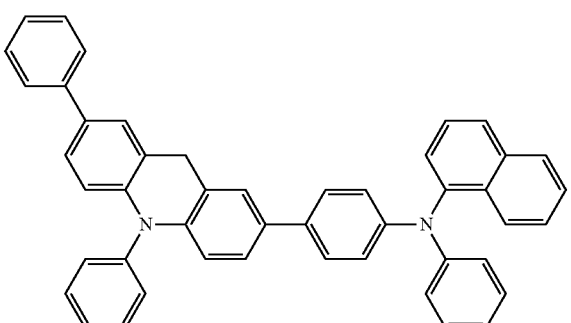
Cpd 40
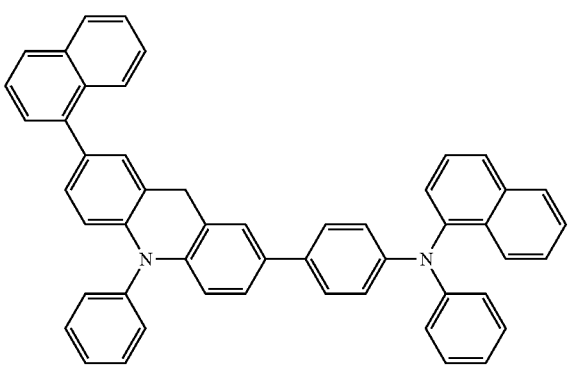
Cpd 41

Cpd 42
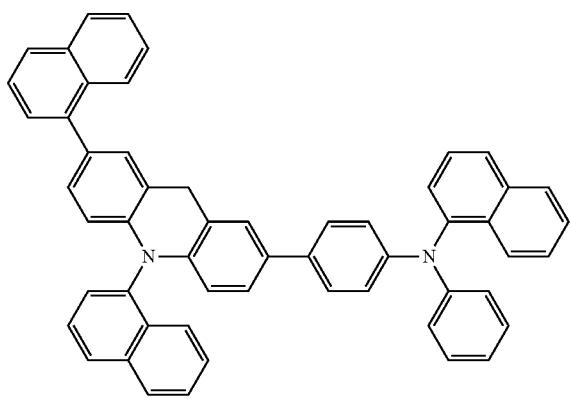
Cpd 43
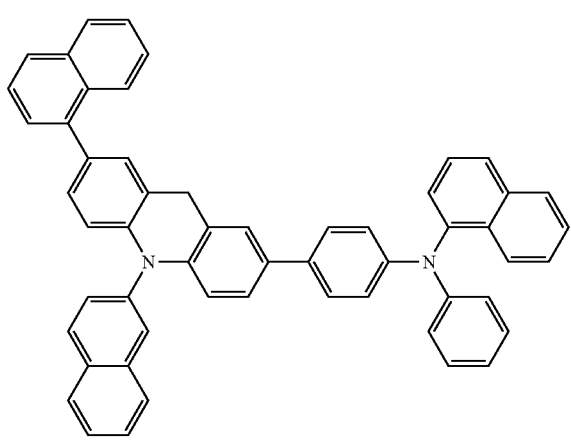
Cpd 44
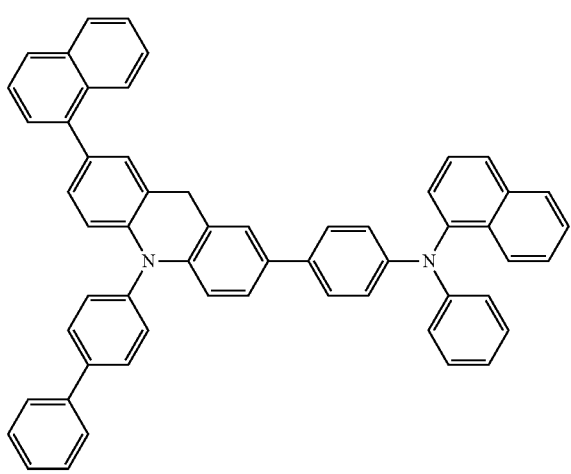
Cpd 45
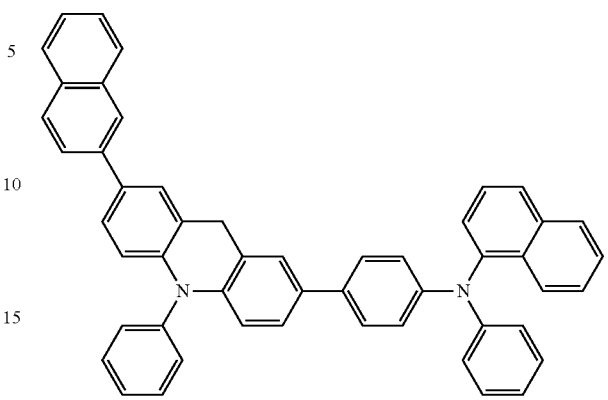
Cpd 46
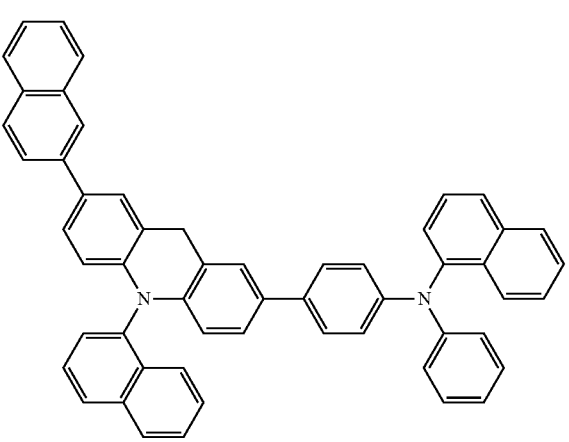
Cpd 47
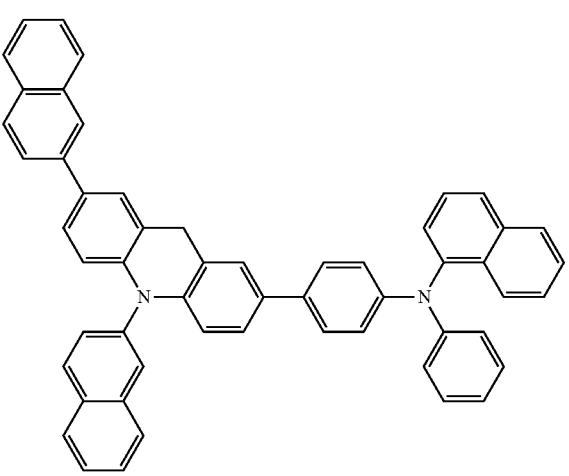

Cpd 48
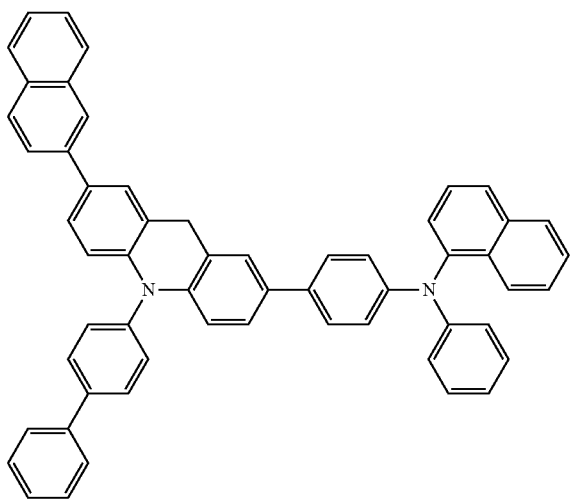
Cpd 49
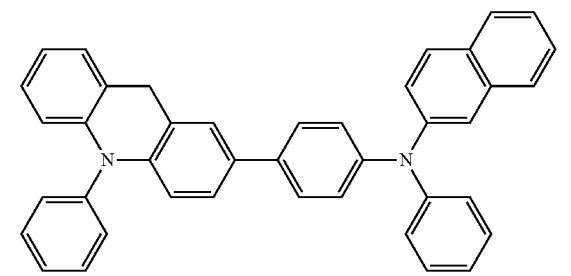
Cpd 50
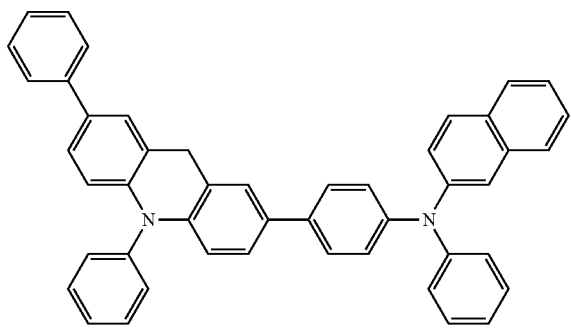
Cpd 51
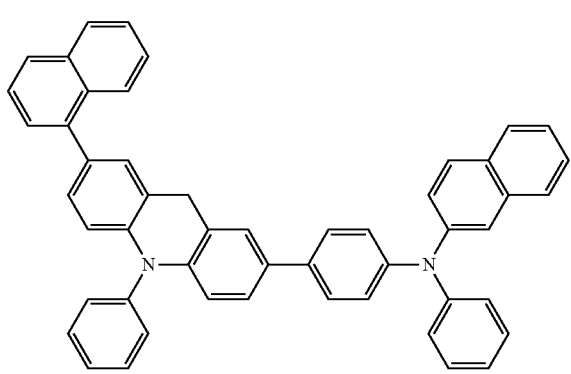
Cpd 52
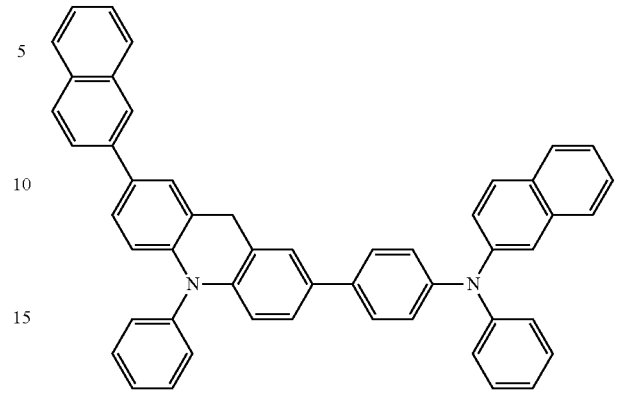
Cpd 53
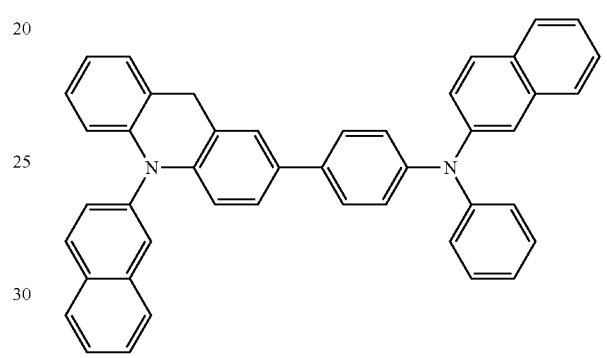
Cpd 54
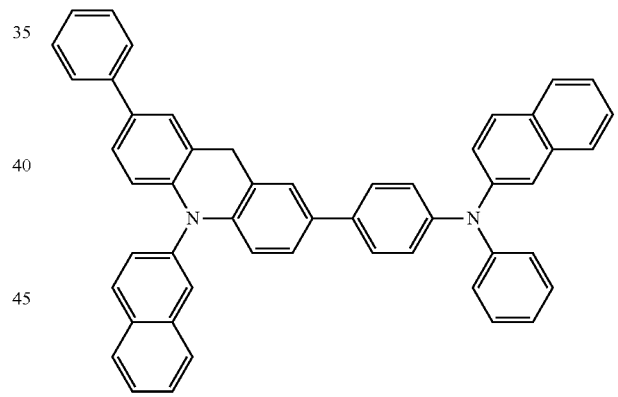
Cpd 55
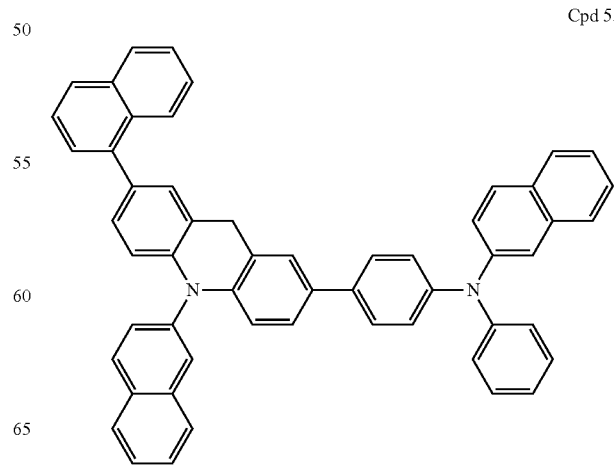

Cpd 56
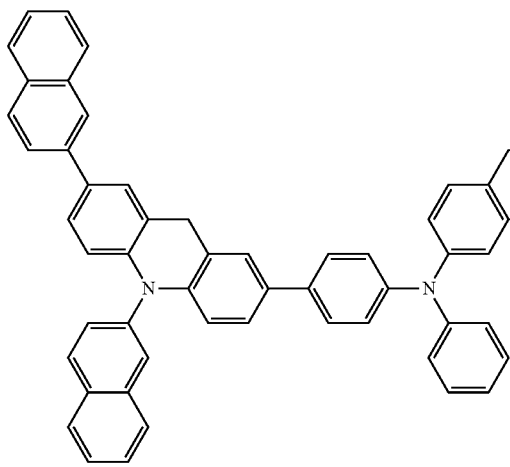
Cpd 57
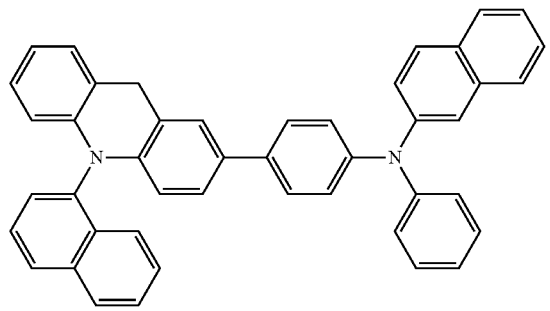
Cpd 58
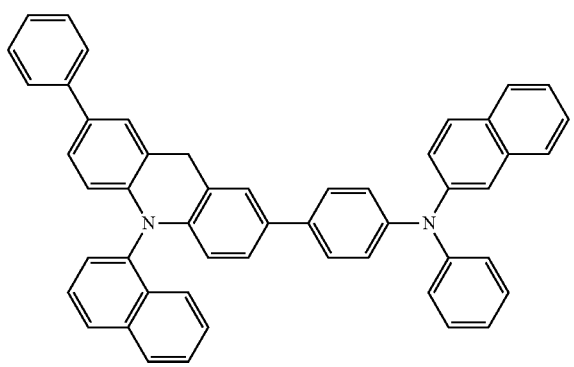
Cpd 59
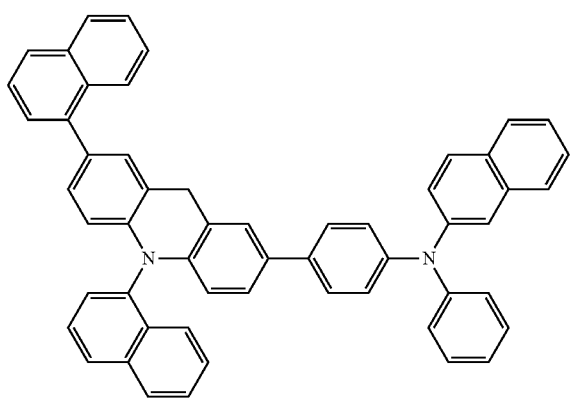
Cpd 60
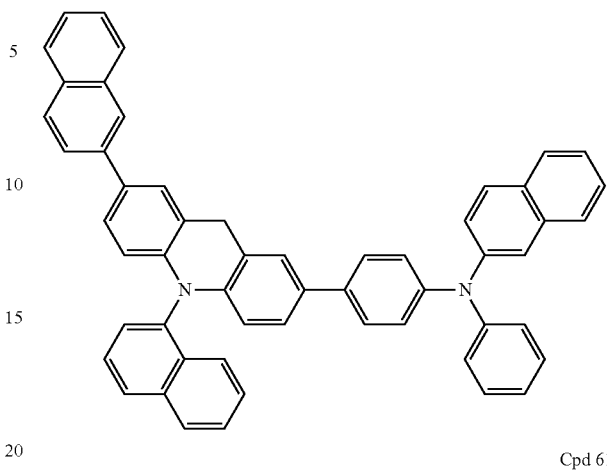
Cpd 61
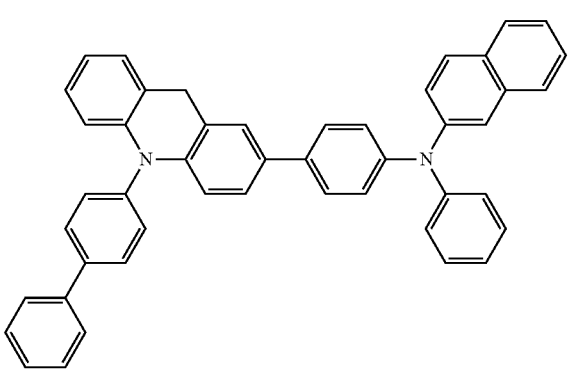
Cpd 62
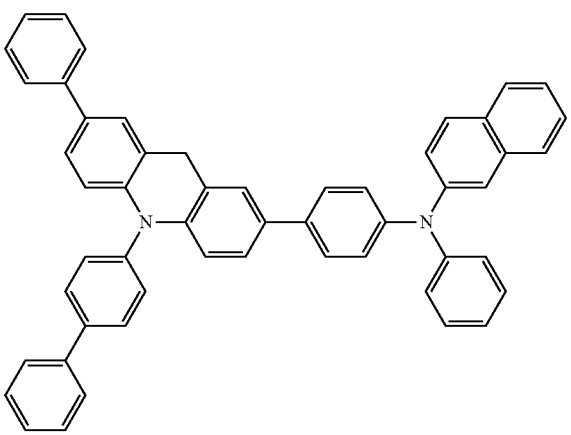

Cpd 63
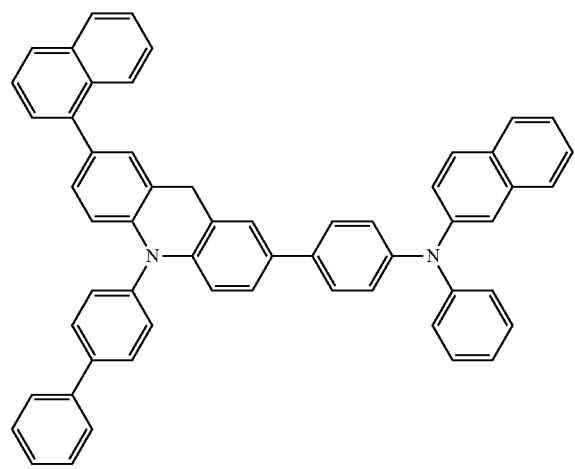
Cpd 64
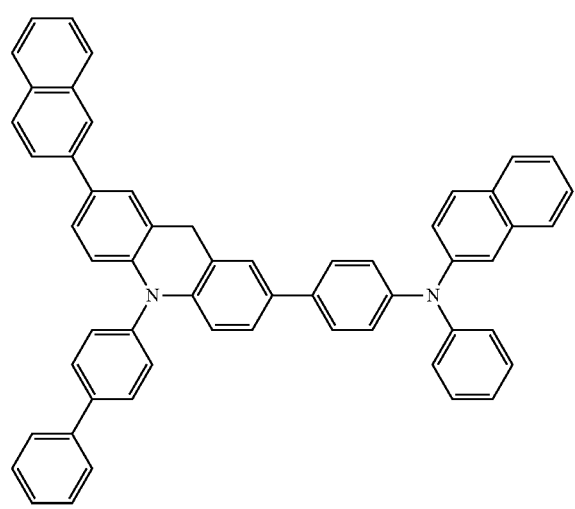
Cpd 65
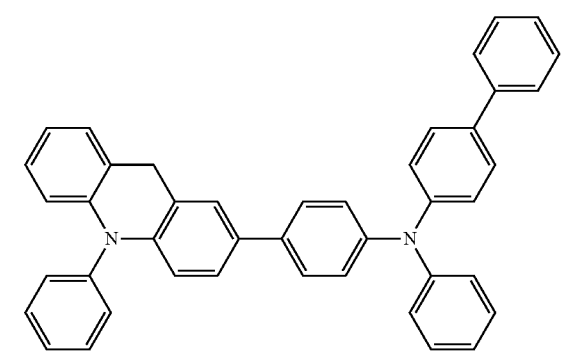
Cpd 66
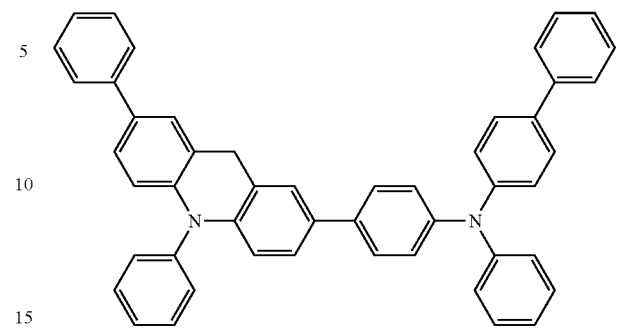
Cpd 67
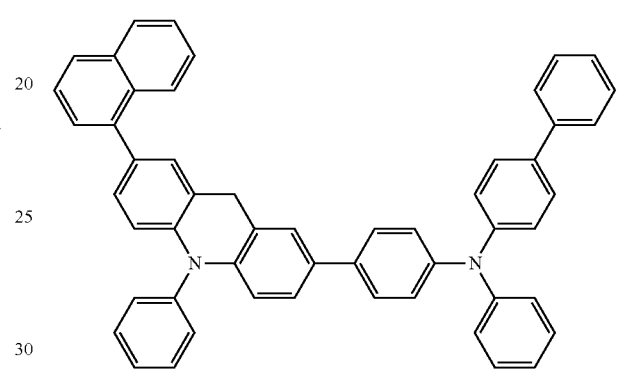
Cpd 68
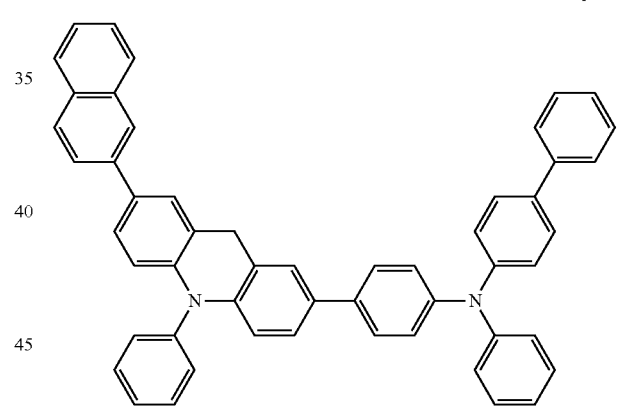
Cpd 69
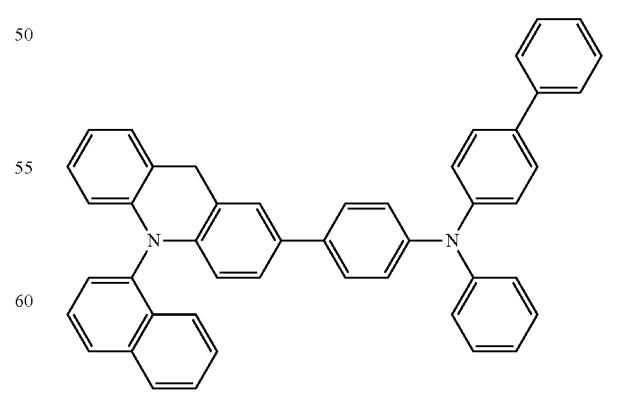

Cpd 70
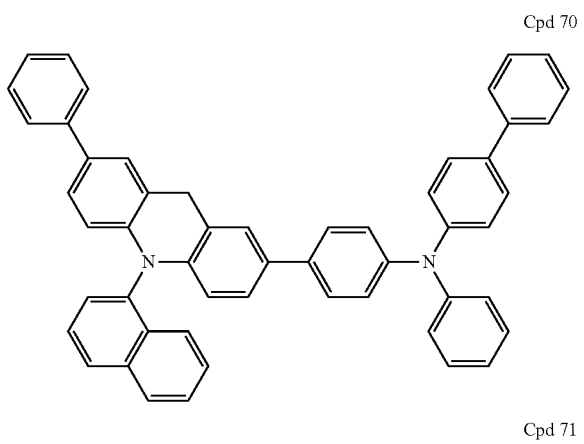
Cpd 73
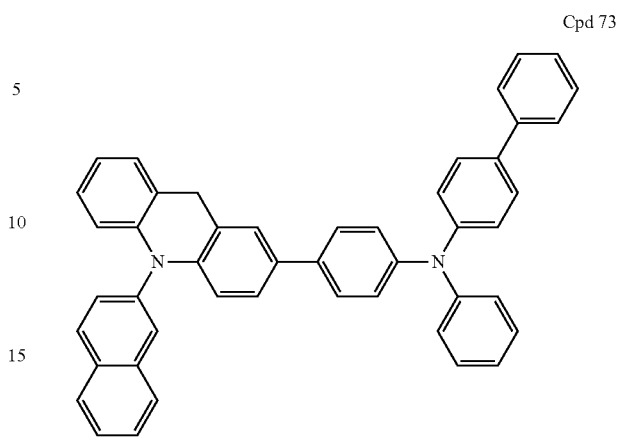
Cpd 71
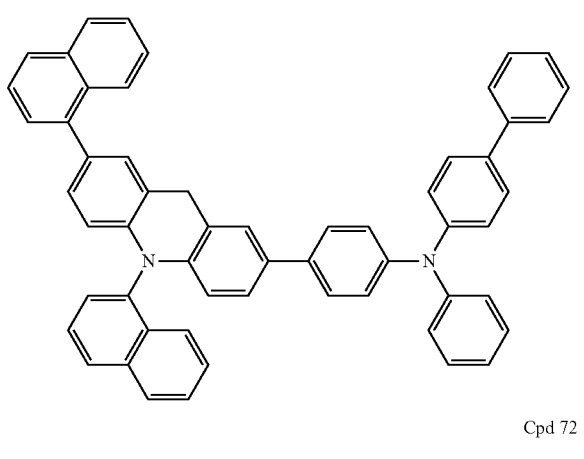
Cpd 74
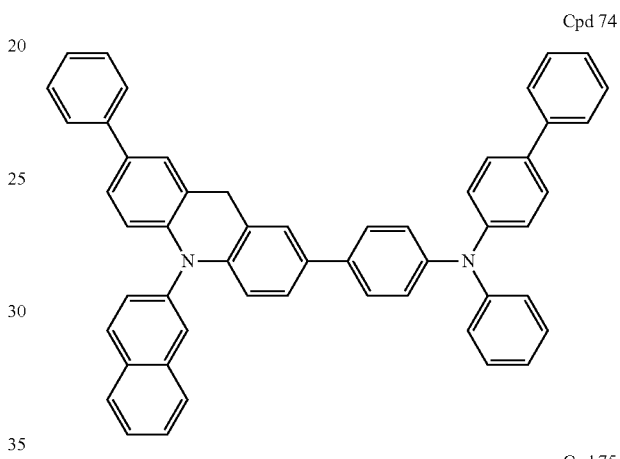
Cpd 72
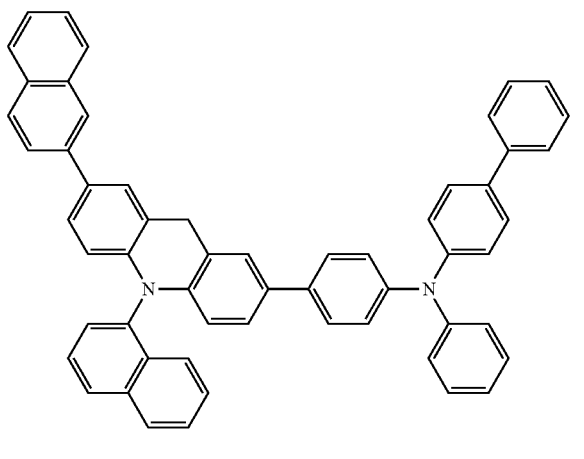
Cpd 75
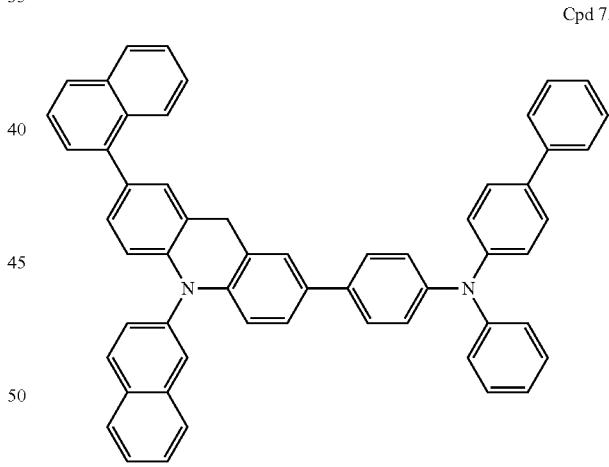

Cpd 76
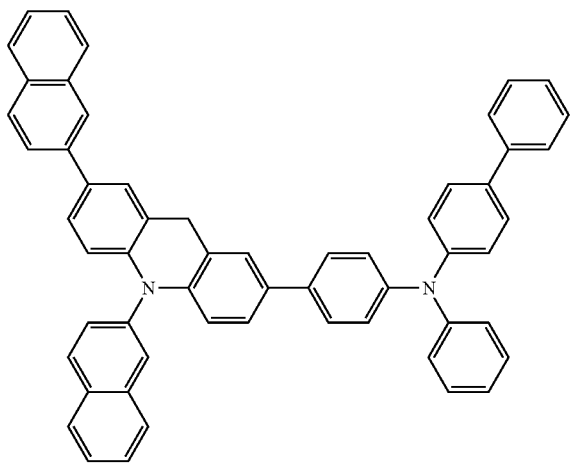
Cpd 79
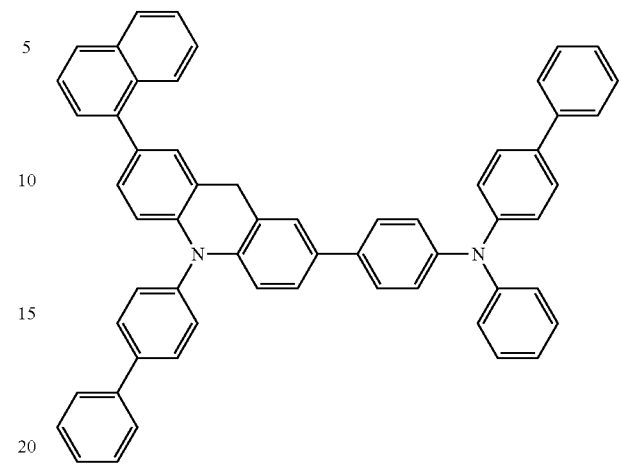
Cpd 77
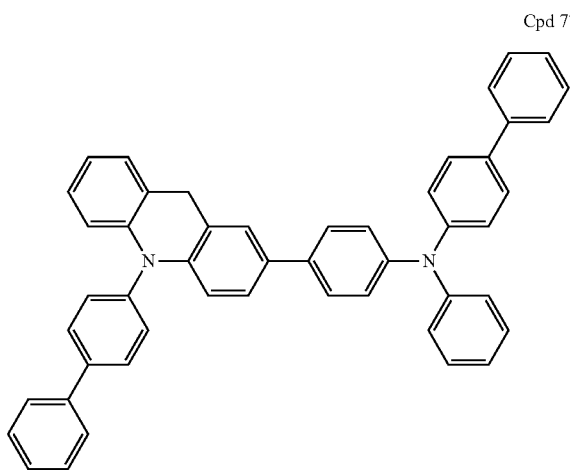
Cpd 80
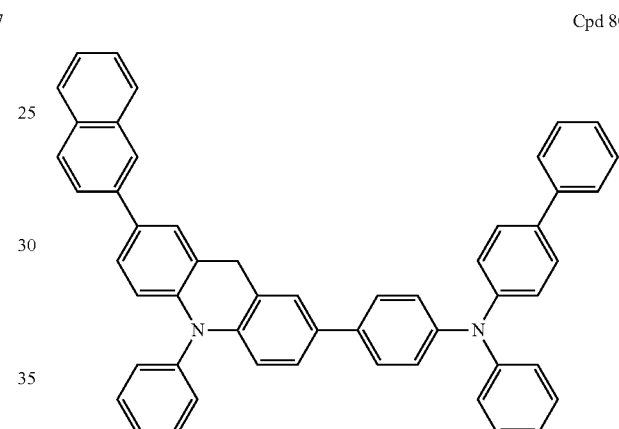
Cpd 78
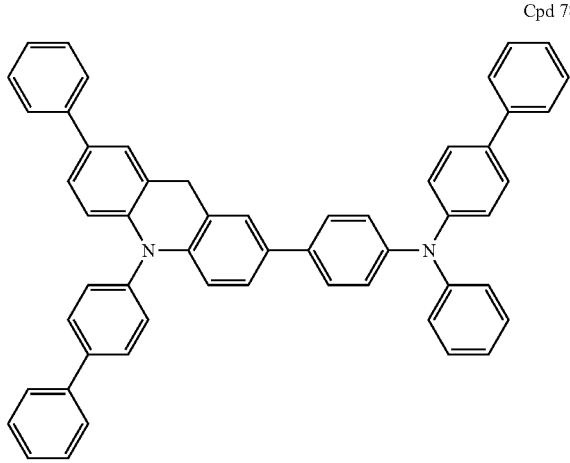
Cpd 81
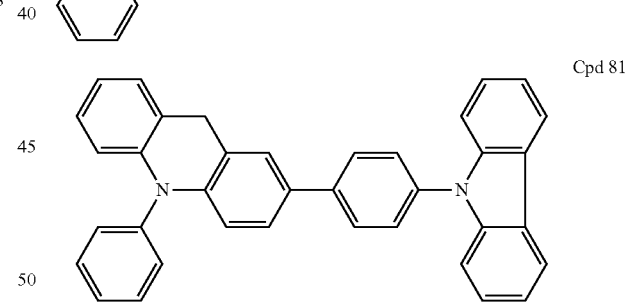
Cpd 82
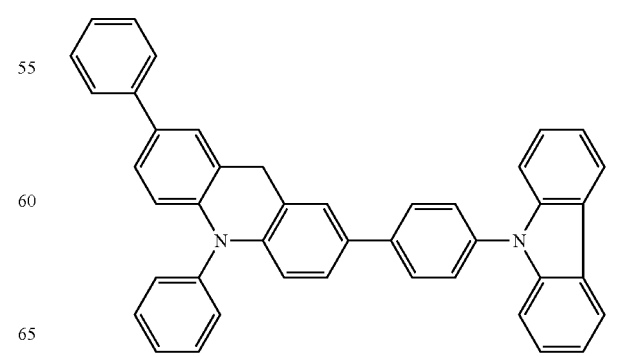

Cpd 83
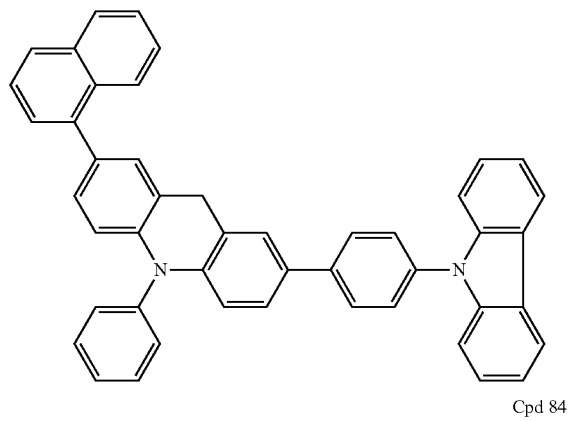
Cpd 84
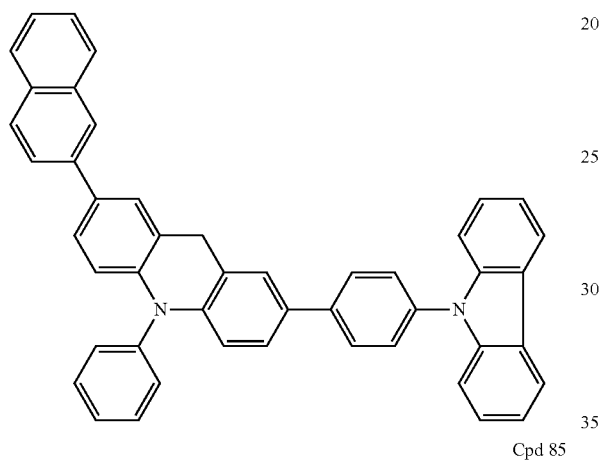
Cpd 85
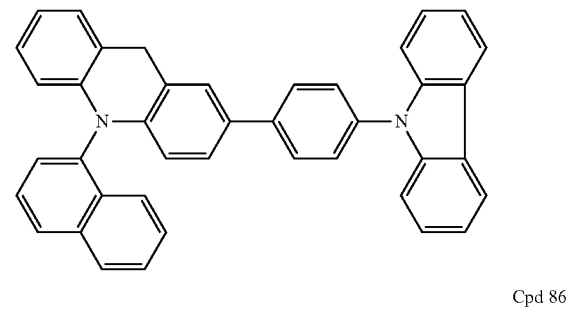
Cpd 86
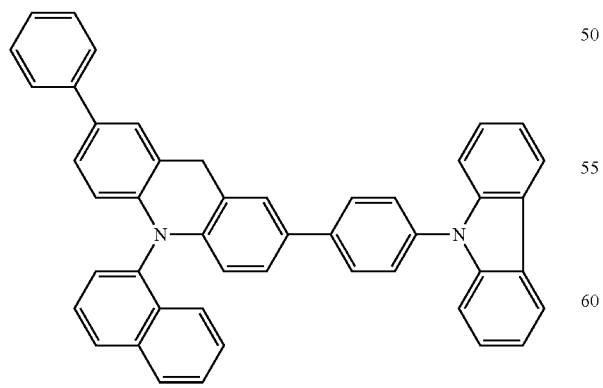
Cpd 87
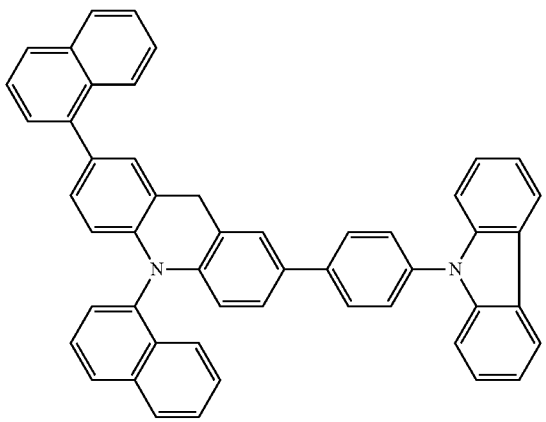
Cpd 88
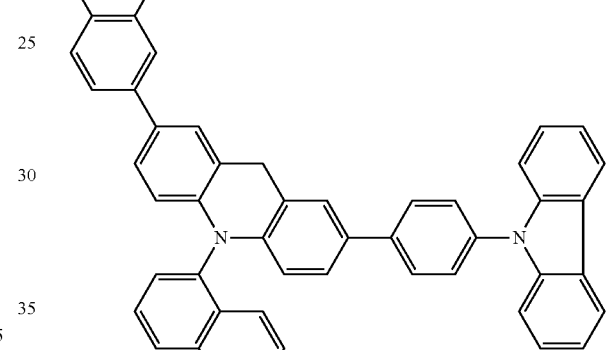
Cpd 89
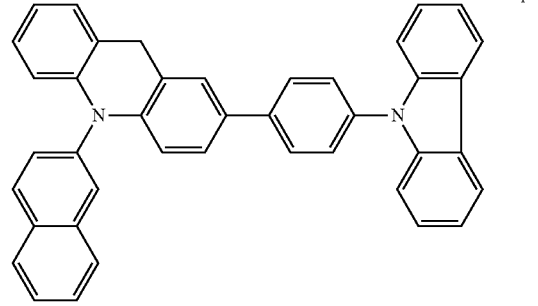

Cpd 90
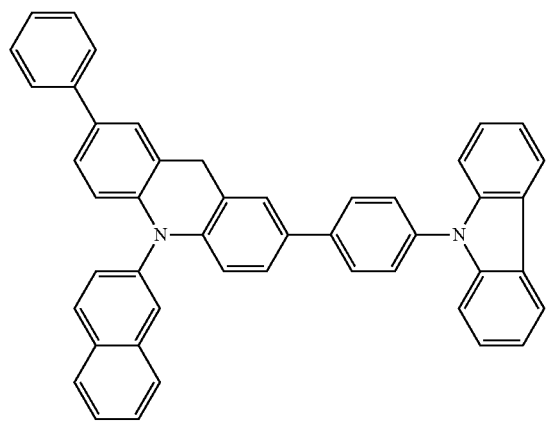
Cpd 91
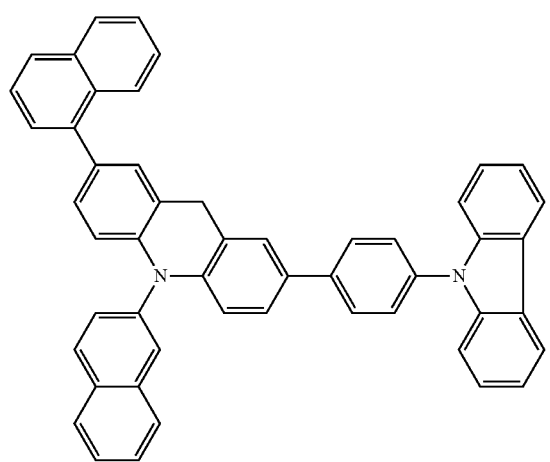
Cpd 92
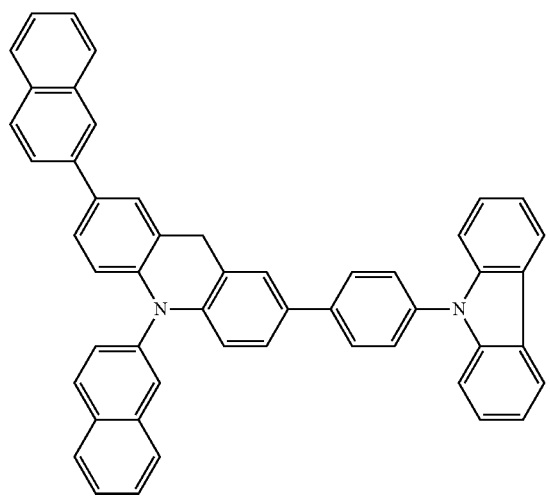
Cpd 93
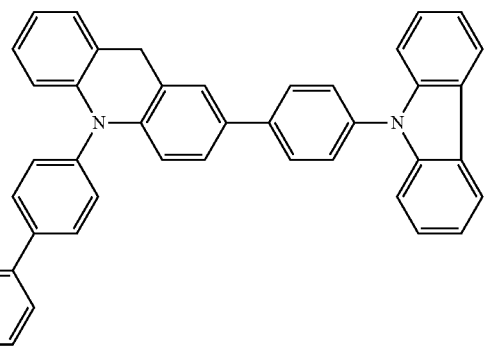
Cpd 94
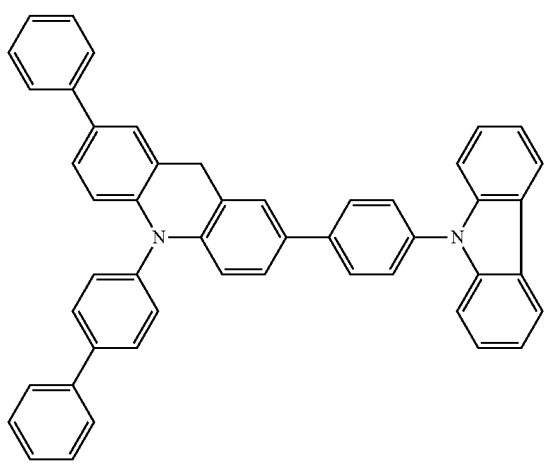
Cpd 95
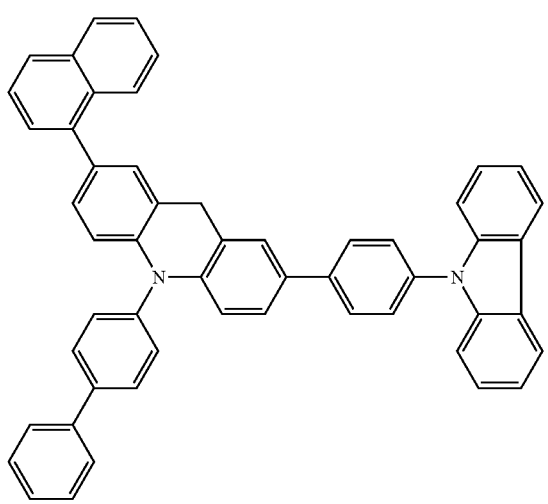

Cpd 96
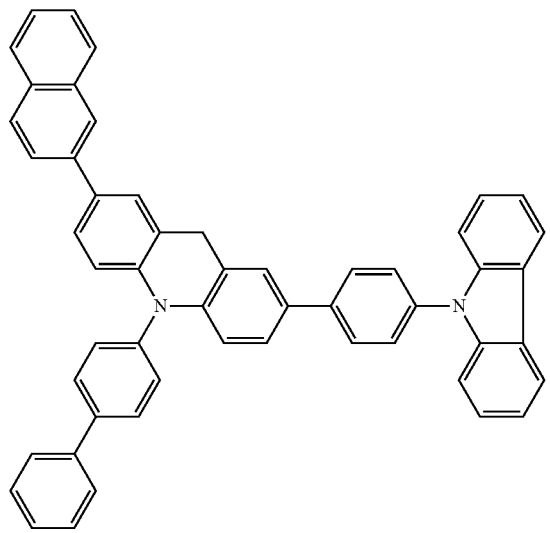
Cpd 100
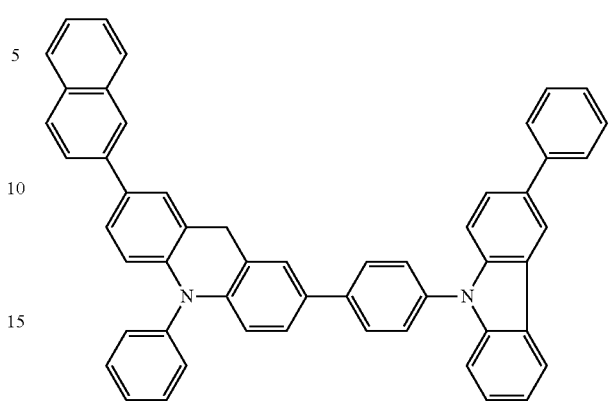
Cpd 97
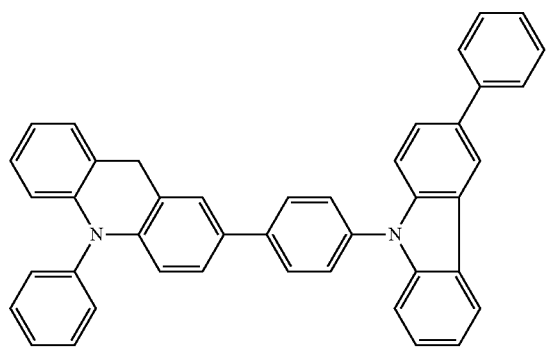
Cpd 101
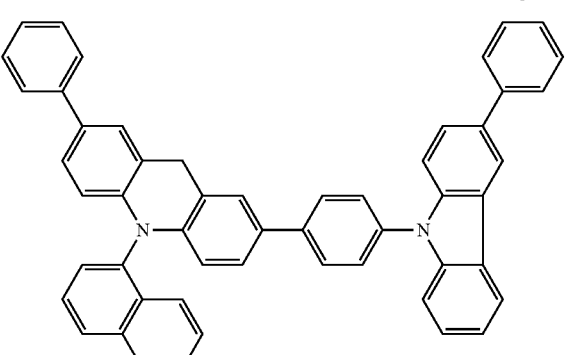
Cpd 98
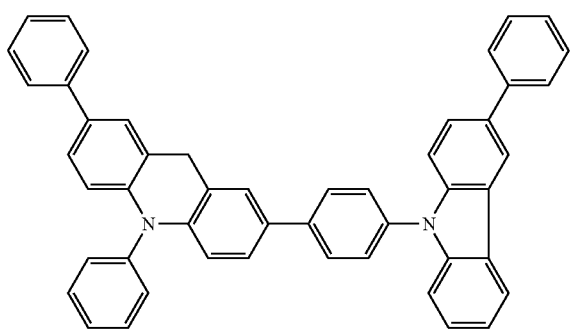
Cpd 102
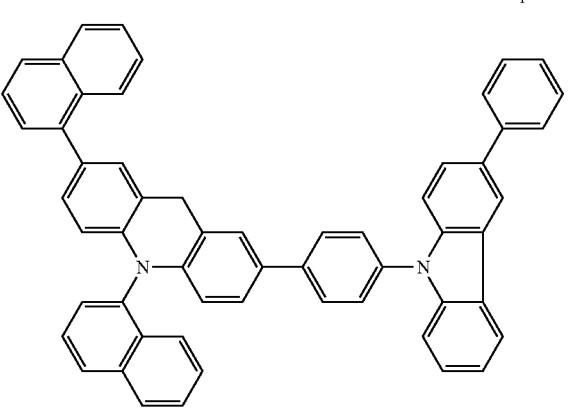
Cpd 99
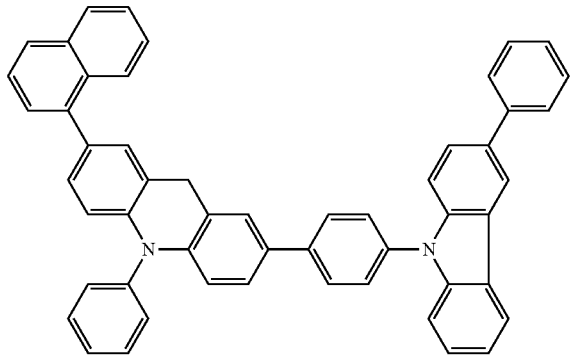
Cpd 103

Cpd 104
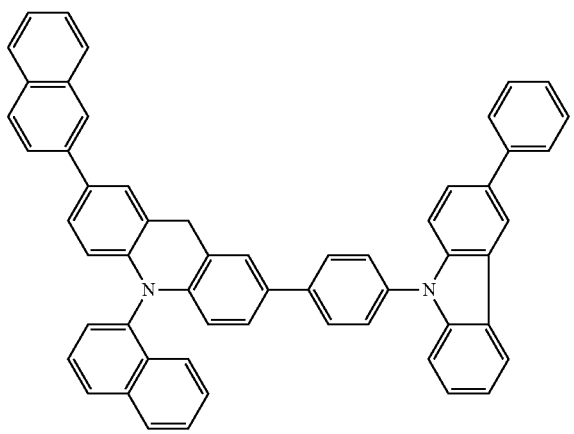
Cpd 105
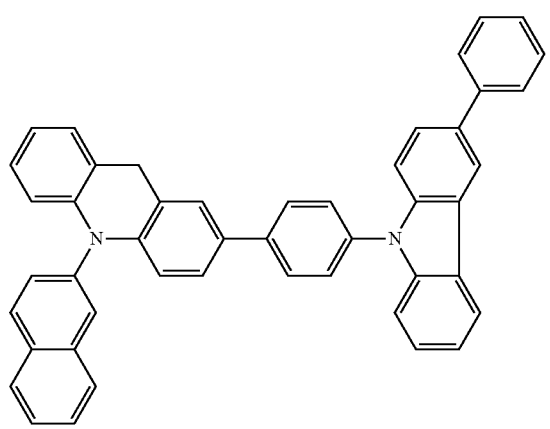
Cpd 106
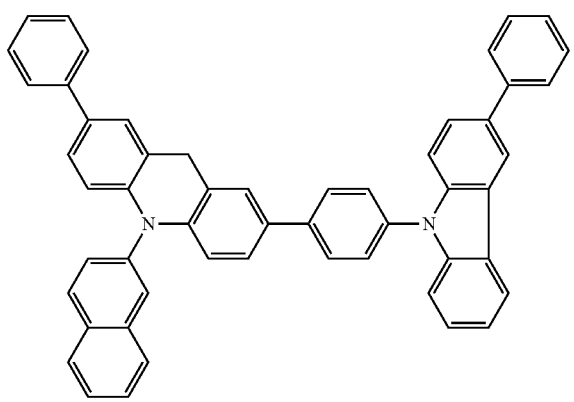
Cpd 107
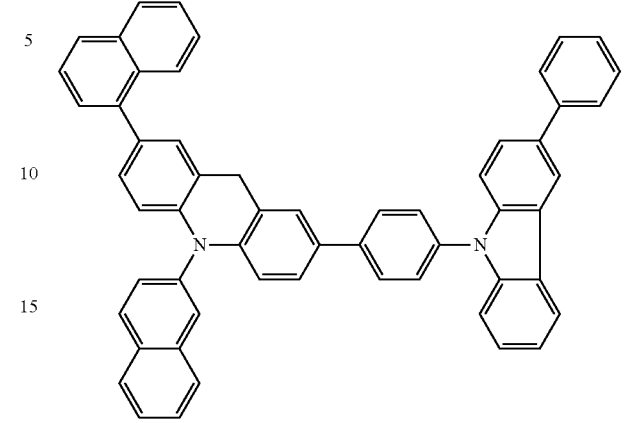
Cpd 108
Cpd 109
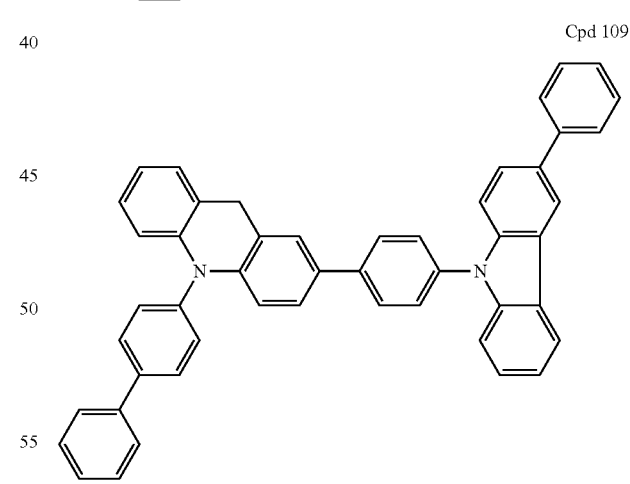

Cpd 110
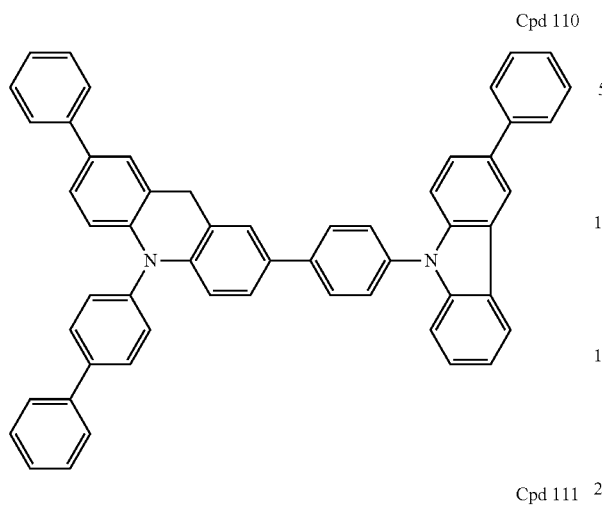
Cpd 111
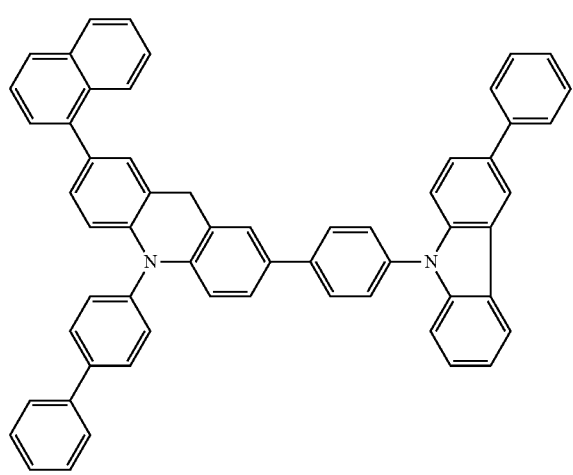
Cpd 112
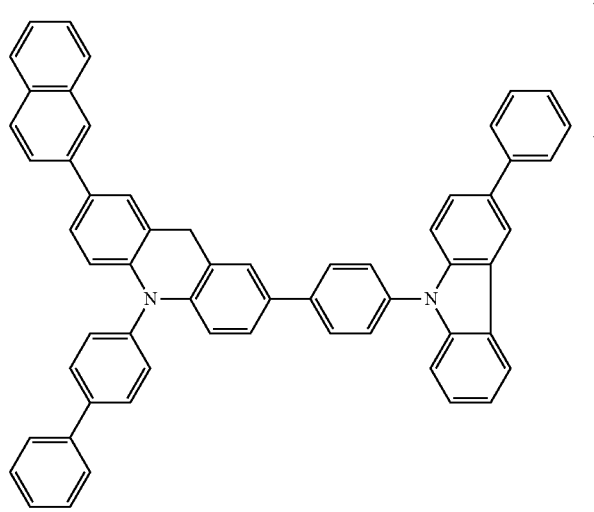
Cpd 113
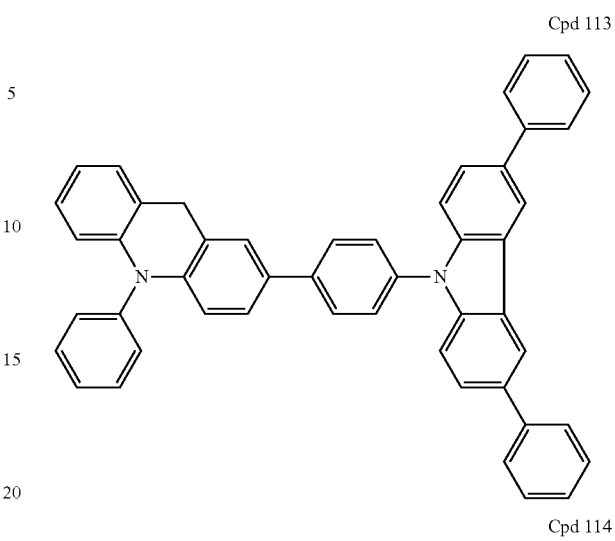
Cpd 114
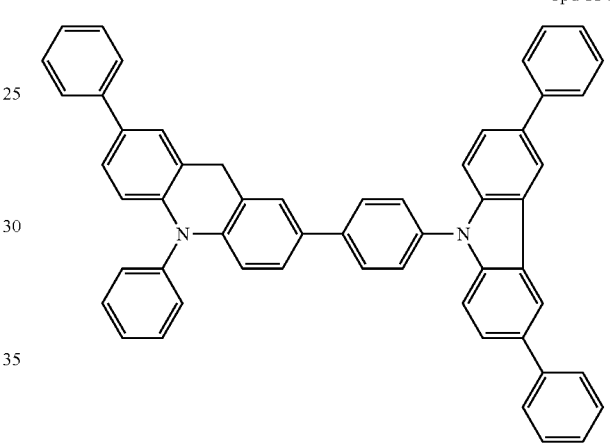
Cpd 115
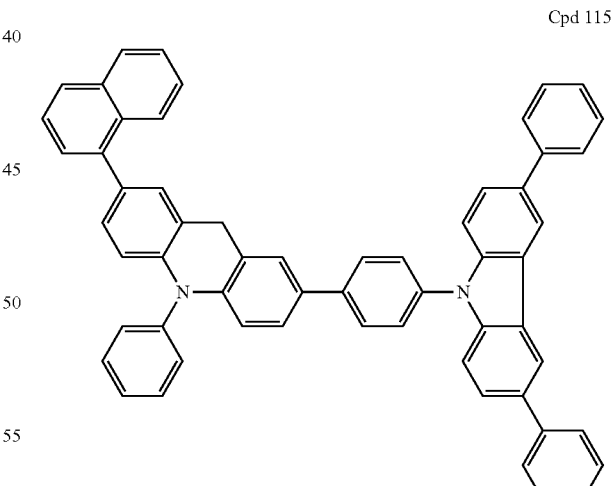

Cpd 116
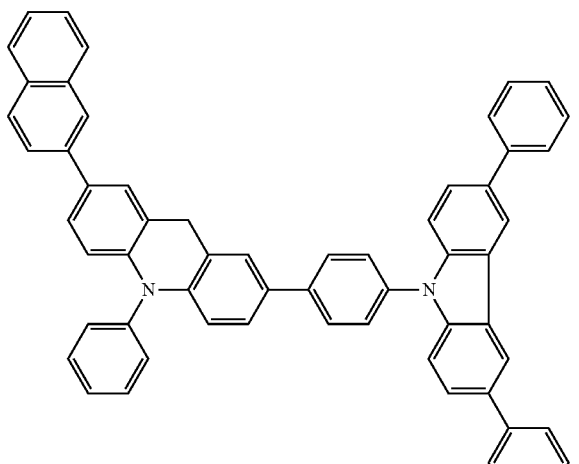
Cpd 119
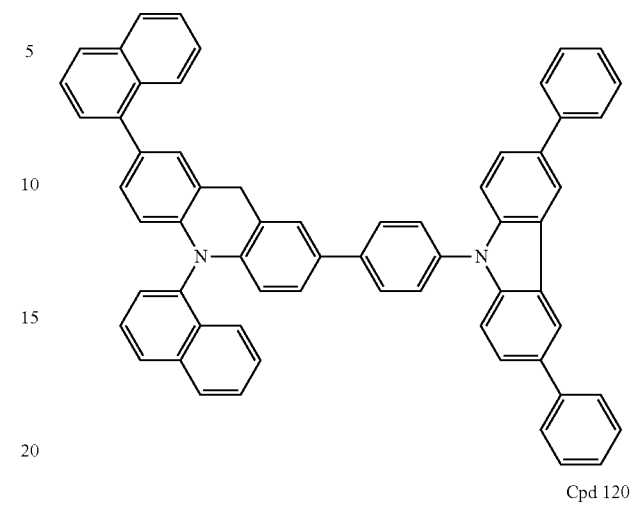
Cpd 117
Cpd 120
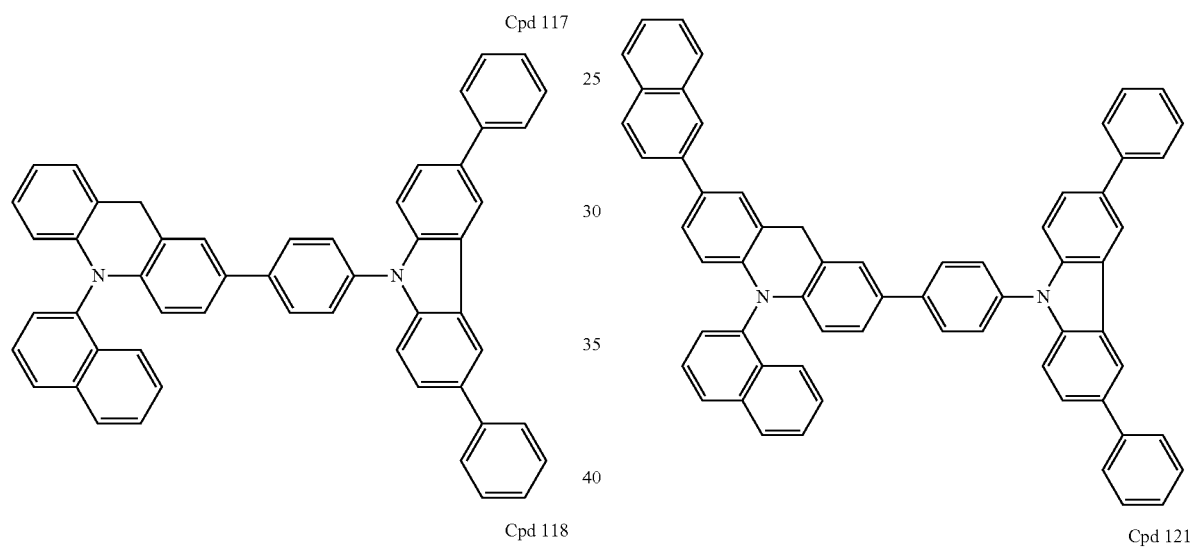
Cpd 118
Cpd 121
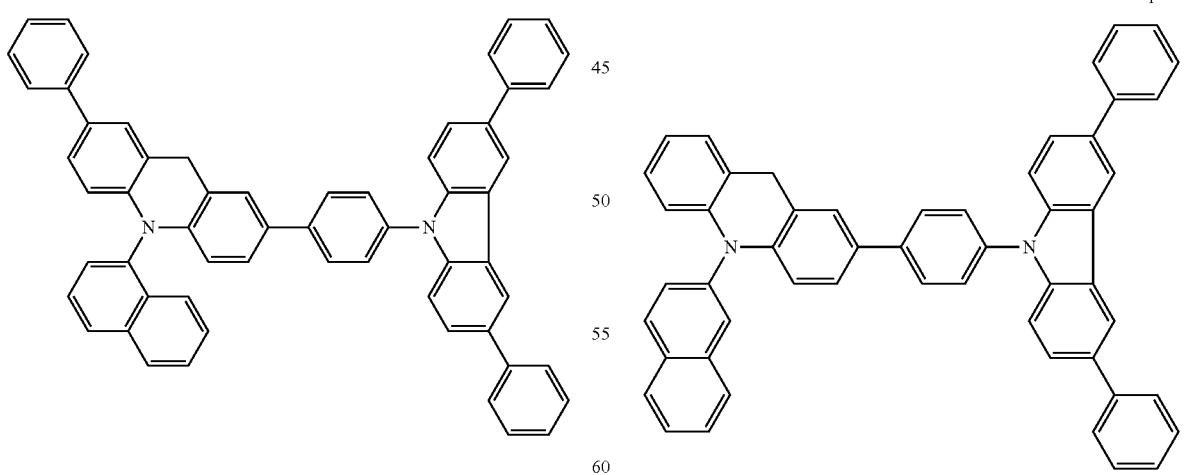

Cpd 122
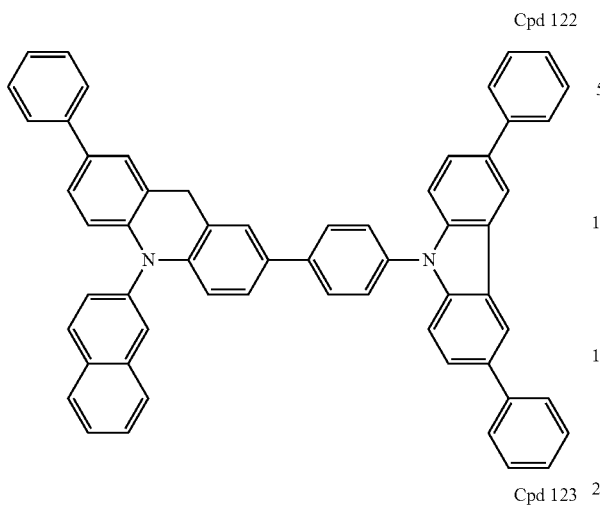
Cpd 123
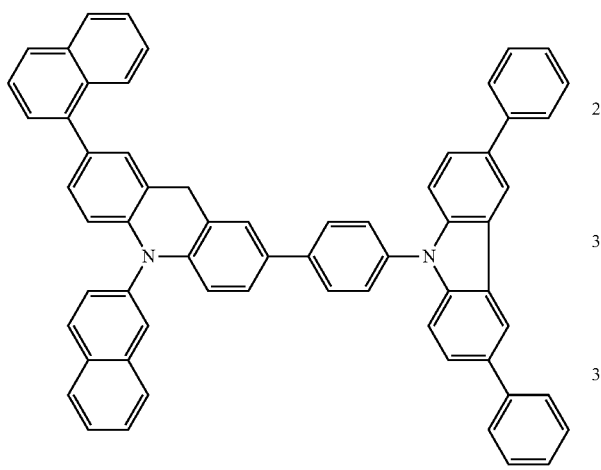
Cpd 124
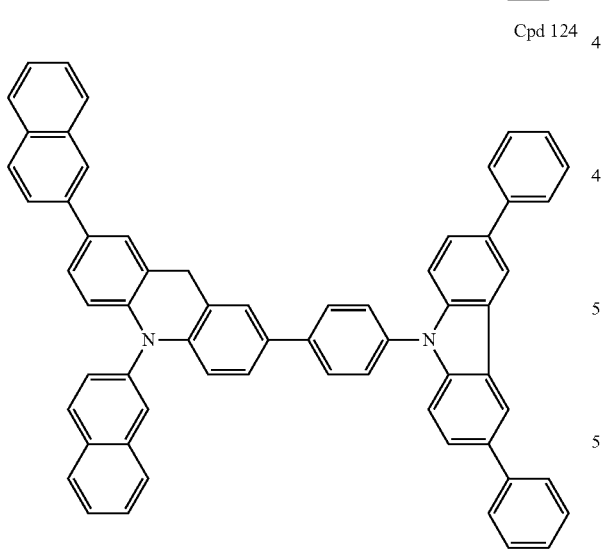
Cpd 125
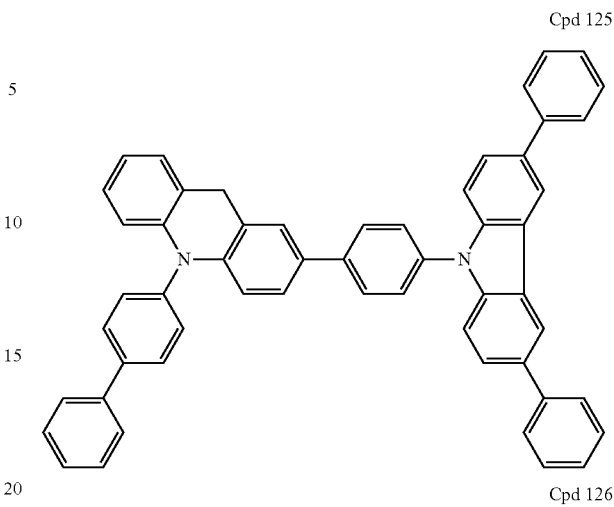
Cpd 126
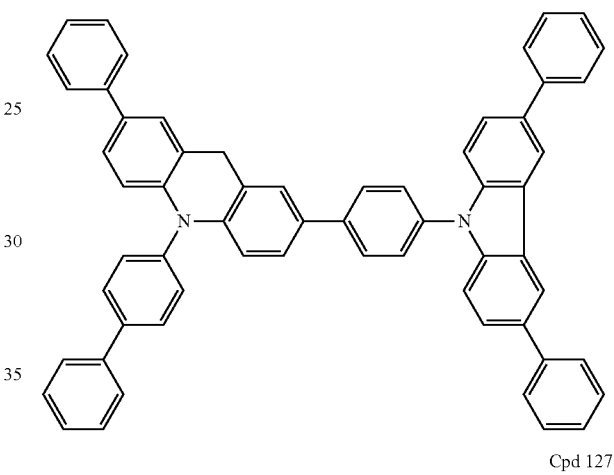
Cpd 127
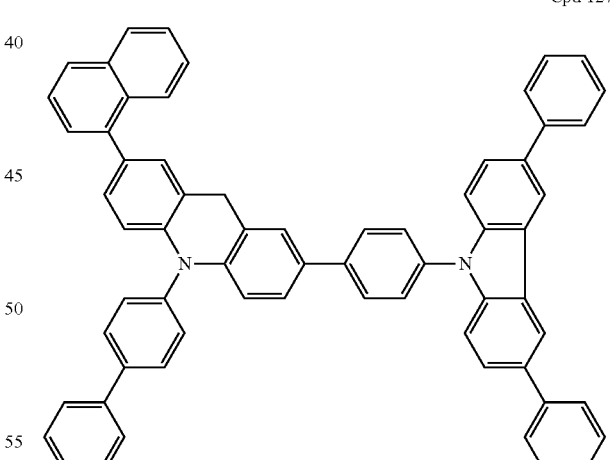

Cpd 128
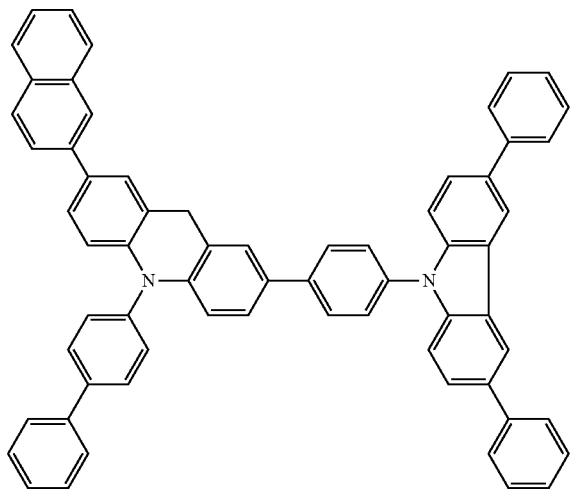
Cpd 129
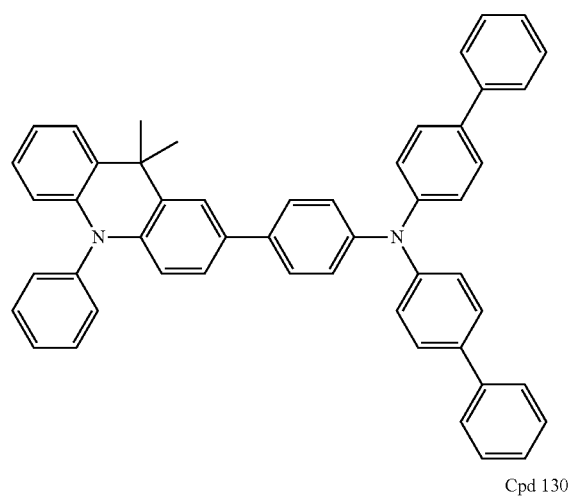
Cpd 130
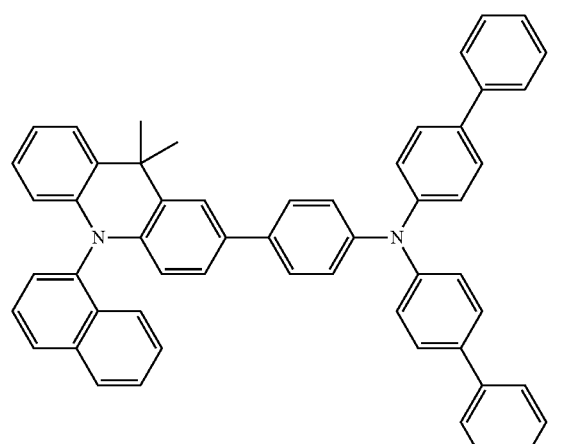
Cpd 131
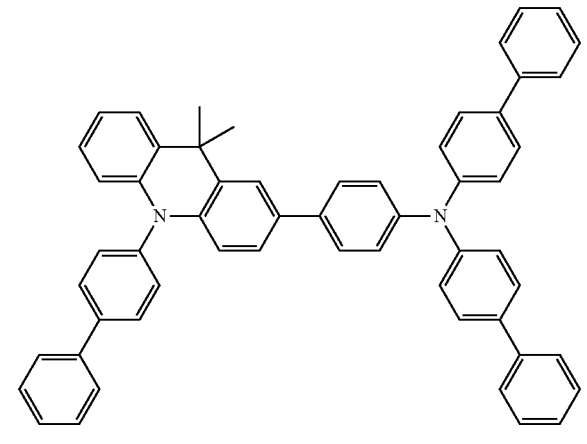
Cpd 132
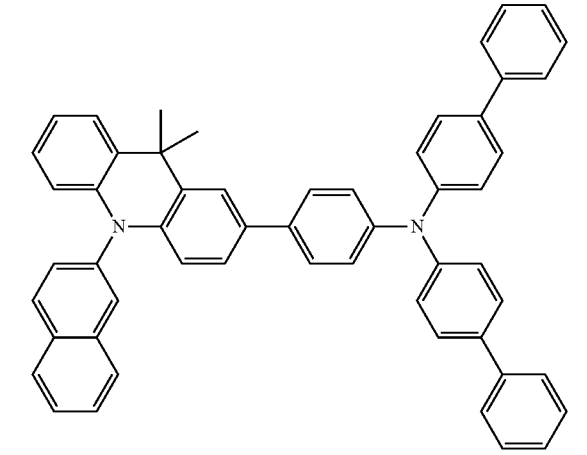
Cpd 133
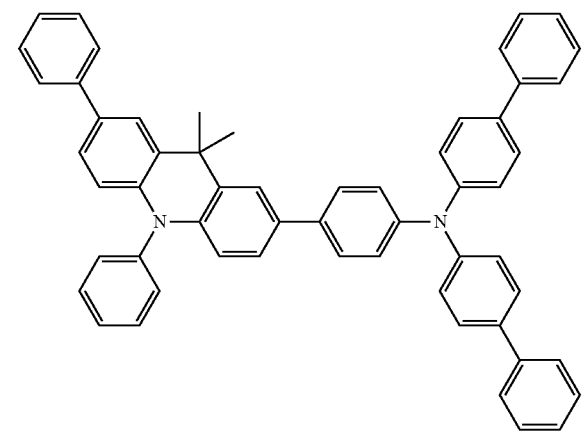

Cpd 134
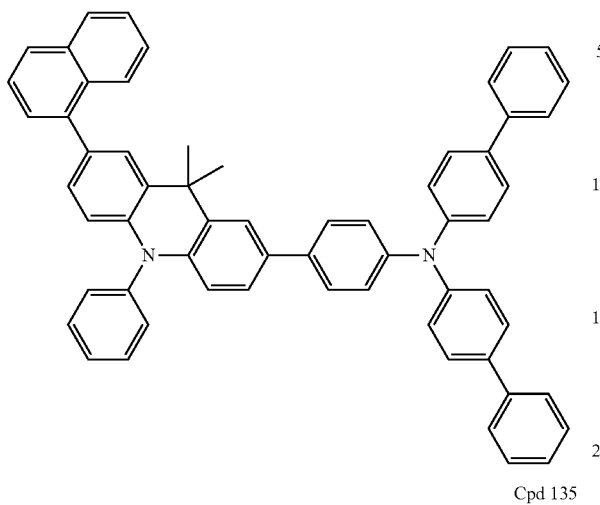
Cpd 135
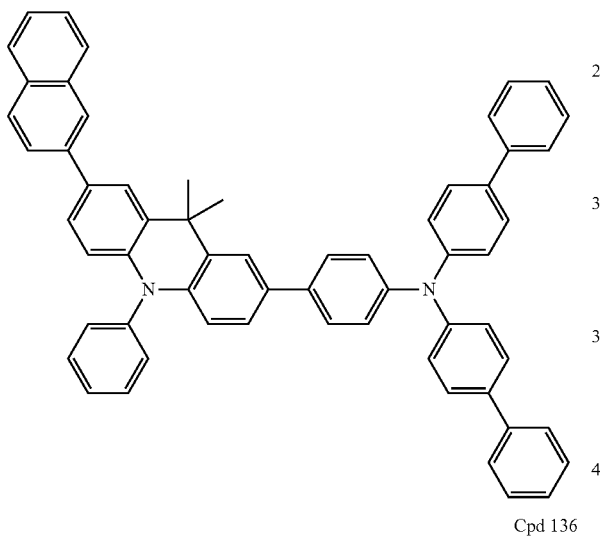
Cpd 136
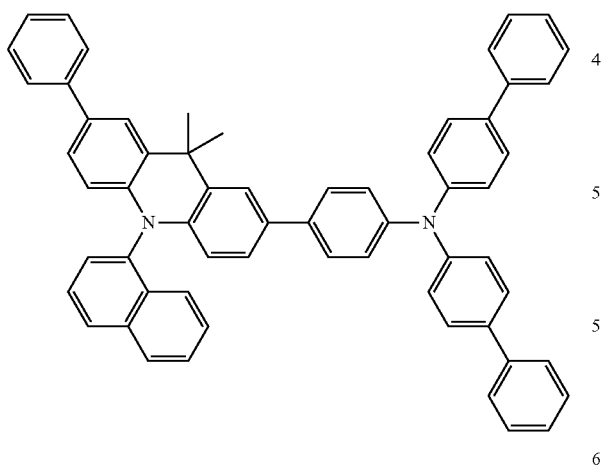
Cpd 137
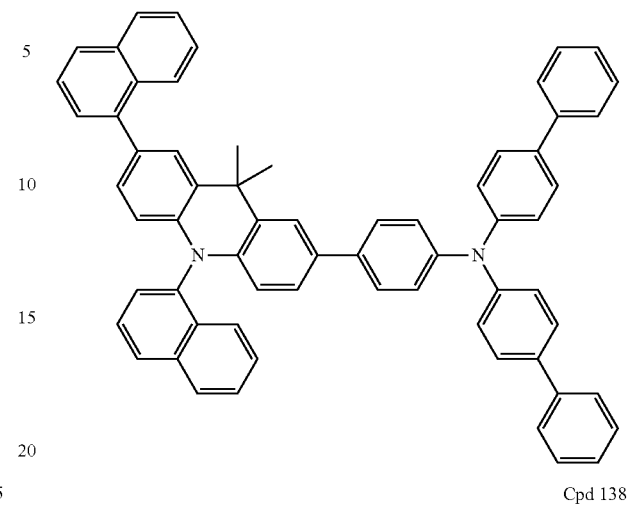
Cpd 138
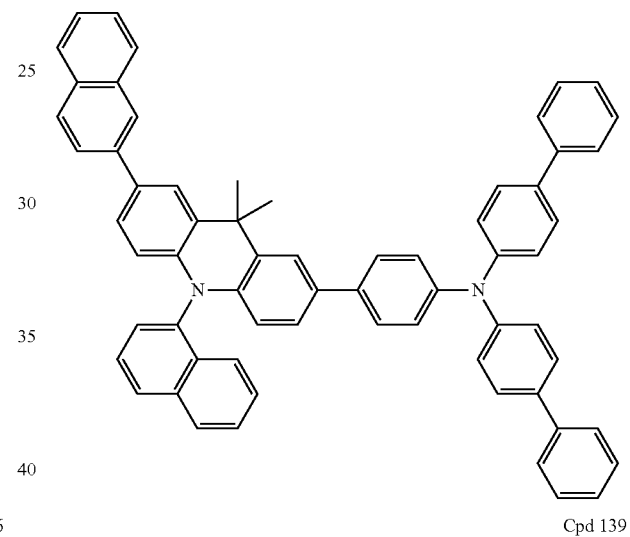
Cpd 139
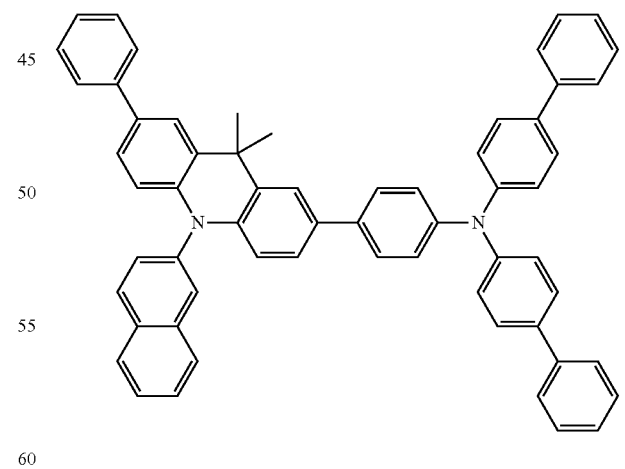

Cpd 140
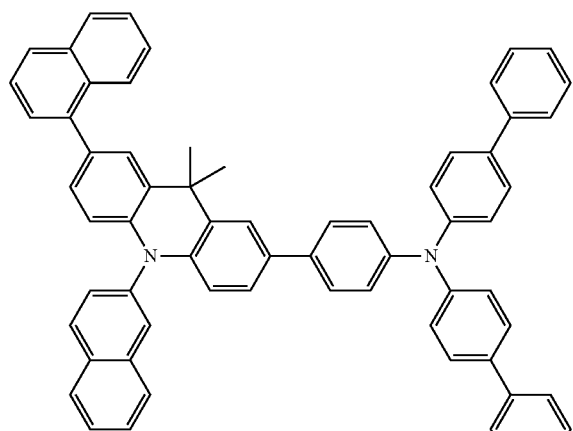
Cpd 141
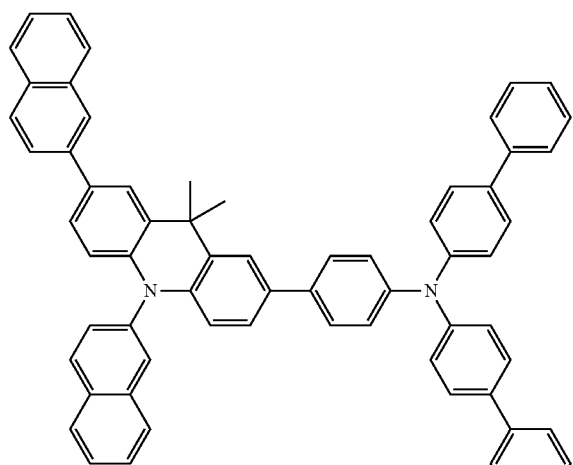
Cpd 142
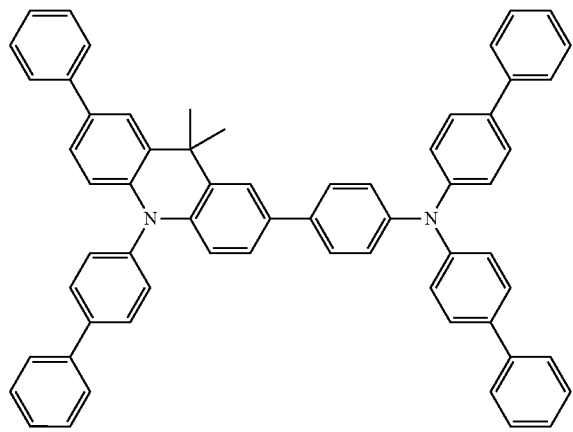
Cpd 143
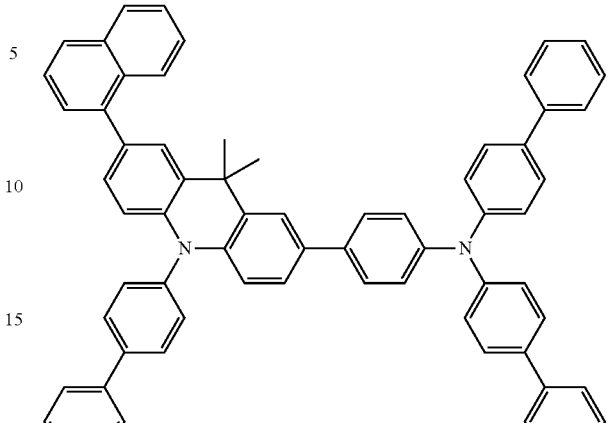
Cpd 144
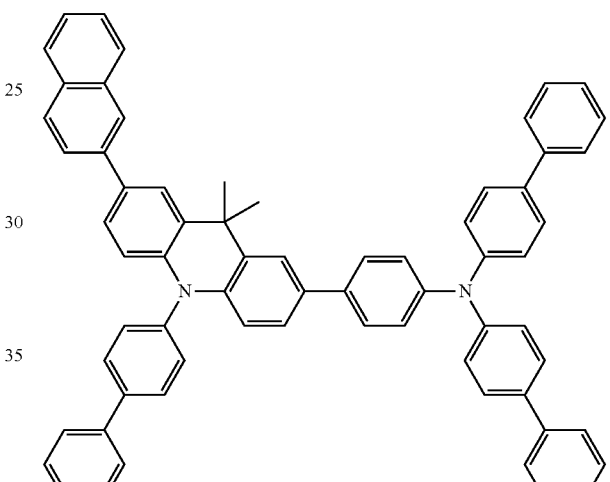
Cpd 145
Cpd 146
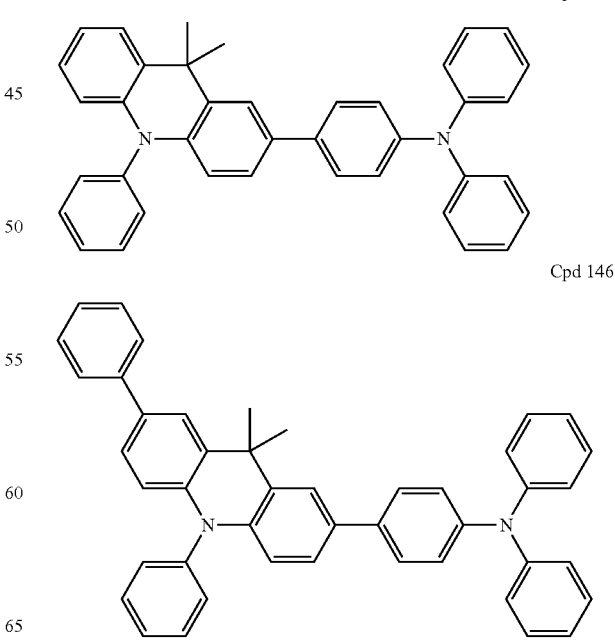

Another aspect of the present invention relates to an organic electro-luminescence device including the inventive compound represented by Formula 1.

Specifically, the inventive organic electro-luminescence device includes (i) an anode; (ii) a cathode; and (iii) one or more organic material layers intervened between the anode and the cathode, wherein at least one layer of the organic material layers includes the compound represented by Formula 1.

In the inventive organic electro-luminescence device, the organic material layer including the compound represented by Formula 1 of the present invention may include one or more of a hole injection layer, a hole transport layer, a light emitting layer, an electron transport layer, and an electron injection layer. Preferably, the organic material layer including the compound represented by Formula 1 may include one or more of a hole injection layer, a hole transport layer, and a light emitting layer.

Also, the organic electro-luminescence device according to the present invention may include, besides the organic material layer including the compound represented by Formula 1 of the present invention, a hole injection layer, a hole transport layer, a light emitting layer, an electron transport layer and/or an electron injection layer.

As a non-limiting example, the inventive organic electro-luminescence device may be structured such that a substrate, an anode, a hole injection layer, a hole transport layer, a light-emitting layer, an electron transport layer and a cathode are sequentially stacked one onto another. Herein, at least one of the hole injection layer, the hole transport layer, and the light emitting layer, includes the compound represented by Formula 1. On the electron transport layer, an electron injection layer may also be disposed.

The inventive organic electro-luminescence device may also be structured such that an anode, one or more organic material layers and a cathode are sequentially stacked, as described above, and an insulating layer or an adhesive layer is interposed between an electrode and an organic material layer.

In the inventive organic electro-luminescence device, the organic material layer including the compound represented by Formula 1 may be formed by vacuum deposition or solution coating. Examples of the solution coating include spin coating, dip coating, doctor blading, inkjet printing, thermal transfer, etc., but are not limited thereto.

In the inventive organic electro-luminescence device, organic material layers and electrodes may be formed of materials known in the art using a method known in the art except that at least one layer of the organic material layers includes the compound represented by Formula 1 of the present invention.

For example, a substrate may be a silicon wafer, quartz, a glass plate, a metal plate, a plastic film or sheet, etc.

An anode material may be a metal such as vanadium, chromium, copper, zinc, or gold, or an alloy thereof; metal oxide such as zinc oxide, indium oxide, indium tin oxide (ITO), indium zinc oxide (IZO); a metal-oxide complex such as ZnO:Al or SnO$_2$:Sb; a conductive polymer such as polythiophene, poly(3-methylthiophene), poly[3,4-(ethylene-1, 2-dioxy)thiophene] (PEDT), polypyrrole and polyaniline; carbon black, etc., but is not limited thereto.

A cathode material may be a metal such as magnesium, calcium, sodium, potassium, titanium, indium, yttrium, lithium, gadolinium, aluminum, silver, tin or lead, or an alloy thereof; a multi-layered material such as LiF/Al or LiO$_2$/Al, but is not limited thereto.

Materials for a hole injection layer, a hole transport layer, a light emitting layer, an electron transport layer, and an electron injection layer are not particularly limited, and may be materials commonly known in the art.

Hereinafter, the present invention will be described more specifically with reference to the following examples. The following examples are only for illustrative purposes and are not intended to limit the scope of the invention.

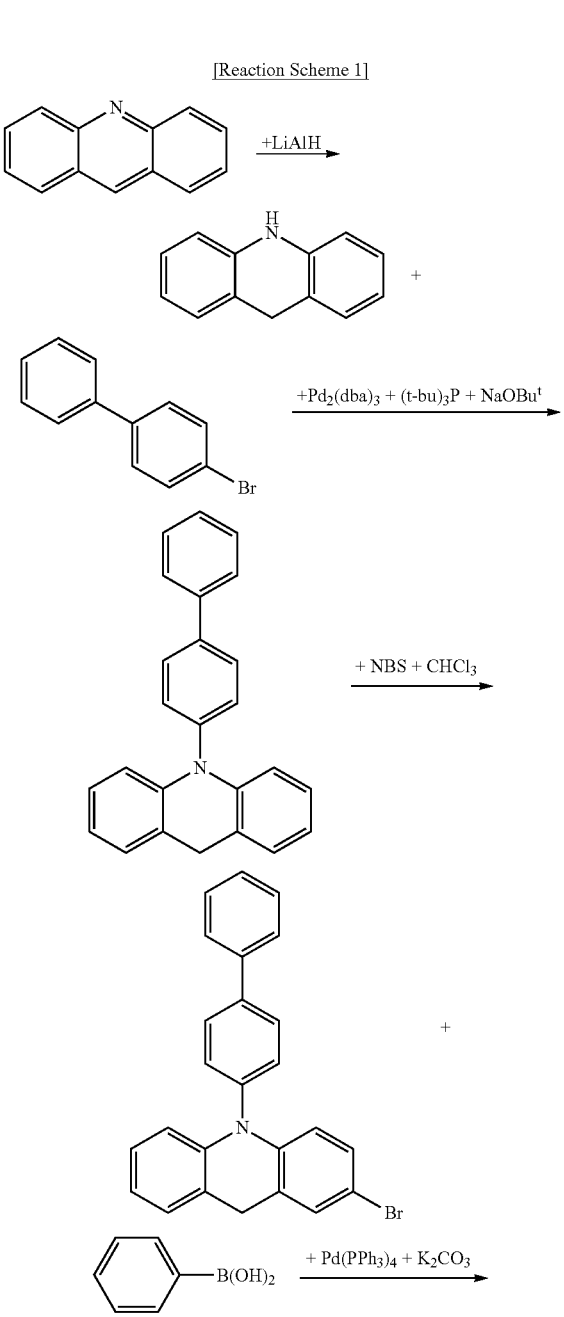

[Reaction Scheme 1]

51
-continued
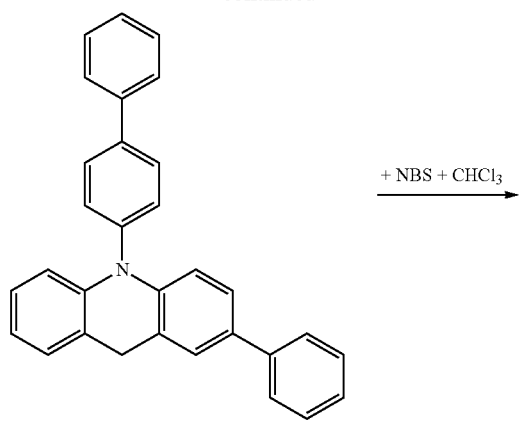
52
-continued
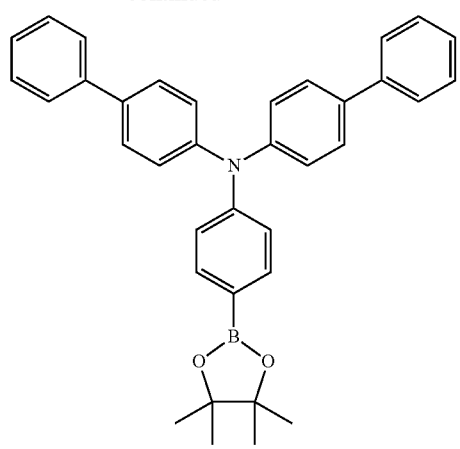
[Reaction Scheme 3]
[Reaction Scheme 2]
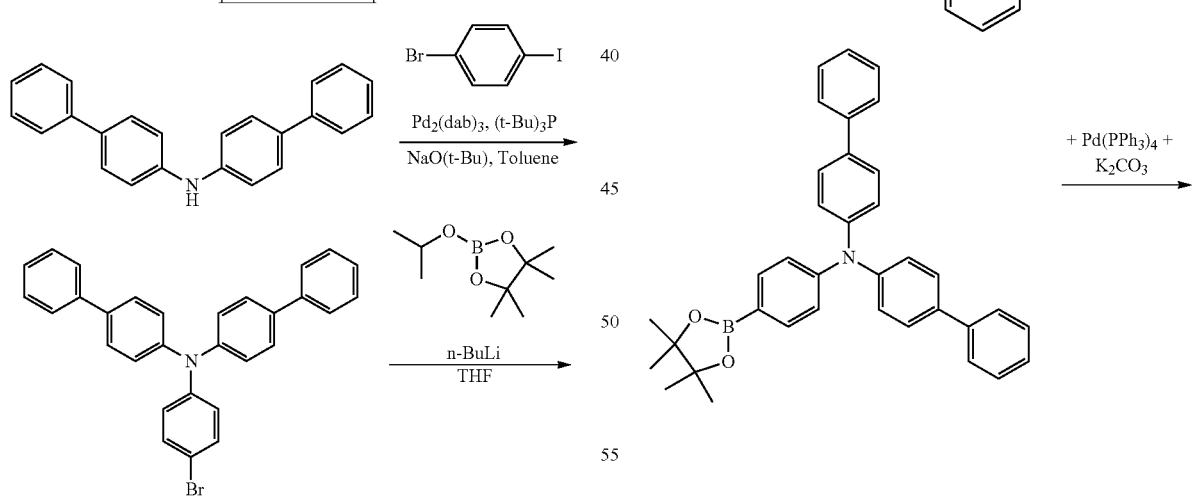
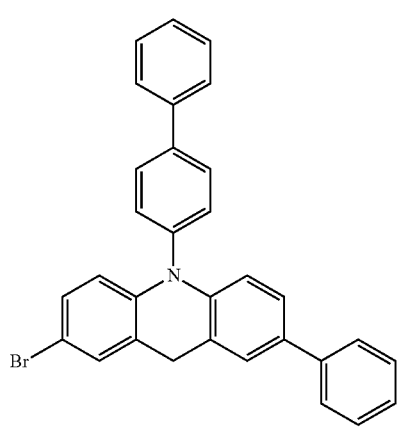 [SMILES: Brc1ccc2c(c1)Cc1cc(-c3ccccc3)ccc1N2c1ccc(-c2ccccc2)cc1]

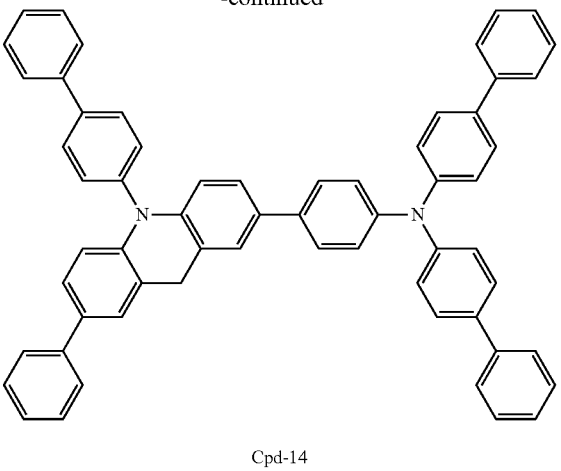

Cpd-14

Synthesis Example 1

Synthesis of Cpd 14 Compound

Synthesis Example 1-1

Synthesis of 9,10-dihydroacridine of Reaction Scheme 1

Under a nitrogen atmosphere, acridine (17.19 g, 95.92 mmol) and THF (300 ml) were introduced into a round-bottom flask. At 0° C., LiAlH$_4$ (14.56 g, 383.66 mmol) was slowly added in halves twice thereto, followed by stirring at room temperature for 4 hours. At 0° C., the resultant product was slowly added with a sodium bicarbonate solution, and then extracted with methylene chloride and distilled water. The extracted layer was dried with sodium sulfate so as to filtrate and concentrate an organic solvent. Then, the resultant product was columned by methylene chloride and hexane (n-Hexane:MC=8:2) so as to obtain a required compound, 9,10-dihydroacridine (white solid, 14 g, 82%).

$^1$H NMR: 3.8 (s, 2H), 4.0 (s, 1H), 6.3 (t, 2H), 6.5 (dd, 2H), 6.8 (m, 4H).

Synthesis Example 1-2

Synthesis of 10-(biphenyl-4-yl)-9,10-dihydroacridine of Reaction Scheme 1

The obtained 9,10-dihydroacridine (11.8 g, 65.2 mmol) and 4-bromobiphenyl (18.2 g, 78.2 mmol) were dissolved in toluene (500 mL). Then, Pd$_2$(dba)$_3$ (1.4 g, 1.3 mmol) was added thereto under a nitrogen atmosphere. Then, NaOBu$^t$ (9.4 g, 97.8 mmol) was added thereto, and (t-Bu)$_3$P (1.6 ml, 2.6 mmol) was introduced to the resultant solution. The resultant mixture was reflux-stirred for 5 hours. The completion of the reaction was identified by a TLC. After the reaction was completed, the mixture was cooled to room temperature. The resultant solution was poured onto a thin silica pad so as to perform a short chromatography, and then was washed with MC. The filtrate was evaporated under a reduced pressure to remove the solvent. The residue was then purified by silica gel column chromatography (methylene chloride/n-hexane (1/10)) to obtain 10-(biphenyl-4-yl)-9,10-dihydroacridine compound (pale yellow solid, 15.3 g, yield 70%).

$^1$H NMR: 3.8 (s, 2H), 6.4 (t, 2H), 6.6 (m, 4H), 6.9 (m, 4H), 7.5 (m, 5H), 7.8 (t, 2H).

Synthesis Example 1-3

Synthesis of 10-(biphenyl-4-yl)-2-bromo-9,10-dihydroacridine of Reaction Scheme 1

The obtained 10-(biphenyl-4-yl)-9,10-dihydroacridine (15.3 g, 45.9 mmol) was added with chloroform (500 ml), and then with bromosuccinimide (9.8 g, 55.1 mmol). The resultant solution was stirred at room temperature for 2 hours. After the reaction was completed, the resultant solution was washed with distilled water. Then, an organic layer was extracted and dried with sodium sulfate so as to remove the solvent. The residue was purified by silica gel column chromatography (methylene chloride/n-hexane (1/20)) to obtain 10-(biphenyl-4-yl)-2-bromo-9,10-dihydroacridine compound (white solid, 14.7 g, yield 77%).

$^1$H NMR: 3.8 (s, 2H), 6.2 (d, 1H), 6.3 (t, 1H), 6.5 (d, 2H), 6.8 (m, 2H), 6.9 (m, 2H), 7.6 (m, 5H), 7.9 (t, 2H).

Synthesis Example 1-4

Synthesis of 10-(biphenyl-4-yl)-2-phenyl-9,10-dihydroacridine of Reaction Scheme 1

10-(biphenyl-4-yl)-2-bromo-9,10-dihydroacridine compound (10 g, 24.3 mmol) was dissolved in toluene (300 mL) under a nitrogen atmosphere. Then, phenyl boronic acid (3.6 g, 29.2 mmol) was added thereto. To the resultant mixture solution, tetrakis triphenyl phosphine palladium (1.1 g, 0.97 mmol) and potassium carbonate (10.1 g, 72.9 mmol) were added. Then, distilled water (40 mL) was added thereto, followed by reflux-stirring for 3 hours. The resultant solution was cooled to about 60° C., and purified by silica gel. Then, a toluene layer was extracted. The extracted organic solvent was concentrated and removed, and methanol was added to produce a solid. Through filtration, a yellowish brown solid was obtained. It was dissolved by methylene chloride, and added with methanol in small amounts so as to obtain required 10-(biphenyl-4-yl)-2-phenyl-9,10-dihydroacridine compound (7.8 g, yield 78%, pale yellow solid).

$^1$H NMR: 3.8 (s, 2H), 6.1 (d, 1H), 6.2 (t, 1H), 6.6 (m, 3H), 6.8 (m, 2H), 7.0 (s, 1H), 7.3 (d, 1H), 7.5 (m, 8H), 7.7 (m, 4H).

Synthesis Example 1-5

Synthesis of 10-(biphenyl-4-yl)-2-bromo-7-phenyl-9,10-dihydroacridine of Reaction Scheme 1

10-(biphenyl-4-yl)-2-phenyl-9,10-dihydroacridine (7.8 g, 19.0 mmol) was added with chloroform (300 ml), and with bromosuccinimide (3.7 g, 21.0 mmol). The resultant solution was stirred at room temperature for 2 hours. After the reaction was completed, the resultant solution was washed with distilled water. Then, an organic layer was extracted and dried with sodium sulfate so as to remove the solvent. The residue was purified by silica gel column chromatography (methylene chloride/n-hexane (1/10)) to obtain 10-(biphenyl-4-yl)-2-bromo-7-phenyl-9,10-dihydroacridine compound (pale yellow solid, 6.5 g, yield 70%).

$^1$H NMR: 3.8 (s, 2H), 6.2 (d, 1H), 6.4 (d, 1H), 6.5 (d, 2H), 6.9 (m, 3H), 7.3 (d, 1H), 7.6 (m, 8H), 7.8 (t, 4H).

Synthesis Example 1-6

Synthesis of N-(biphenyl-4-yl)-N-(4-bromophenyl) biphenyl-4-amine of Reaction Scheme 2

4,4'-bis(biphenylamine) (50 g, 0.182 mol) and 1-Bromo-4-iodobenzene (62.6 g, 0.364 mol) were dissolved in toluene (700 ml). Then, $Pd_2(dba)_3$ (5 g, 5.4 mmol), tri-tert-butylphosphine (2.2 g, 11 mmol), and sodium-tert-butoxide (21 g, 0.22 mol) was introduced into a 1 L RBF, followed by heat-stirring for 3 hours. After the reaction was completed, the resultant solution was washed with distilled water, and purified with column chromatography to obtain N-(biphenyl-4-yl)-N-(4-bromophenyl)biphenyl-4-amine (white solid, 56 g, yield 65%).

$^1$H NMR: 6.3 (d, 2H), 6.5 (t, 4H), 7.2 (t, 2H), 7.5 (m, 10H), 7.8 (t, 4H).

Synthesis Example 1-7

Synthesis of N-(biphenyl-4-yl)-N-(4-(4,4,5,5-tetramethyl-1,3,2-dioxaborolan-2-yl)phenyl)biphenyl-4-amine of Reaction Scheme 2

N-(biphenyl-4-yl)-N-(4-bromophenyl)biphenyl-4-amine (56 g, 0.117 mol) was introduced into a 2 L RBF, and dissolved in THF (600 ml). Then, the temperature was maintained at −78° C. for about 30 minutes. Then, n-BuLi (1.6M in Hex) (90 ml, 0.141 mol) was slowly added thereto. After 1 hour, 2-isopropoxy-4,4,5,5-tetramethyl-1,3,2-dioxaborolane (26.2 g, 0.141 mol) was added thereto, followed by heat-stirring at room temperature for 12 hours. After the reaction was completed, the resultant solution was sufficiently washed with distilled water and Brain, and purified through column chromatography to obtain N-(biphenyl-4-yl)-N-(4-(4,4,5,5-tetramethyl-1,3,2-dioxaborolan-2-yl)phenyl)biphenyl-4-amine (white solid, 20 g, yield 33%).

$^1$H NMR: 1.3 (s, 12H), 6.5 (m, 6H), 7.0 (d, 2H), 7.5 (m, 10H), 7.7 (t, 4H).

Synthesis Example 1-8

Synthesis of N-(biphenyl-4-yl)-N-(4-(10-(biphenyl-4-yl)-7-phenyl-9,10-dihydroacridin-2-yl)phenyl) biphenyl-4-amine (Cpd-14) of Reaction Scheme 3

10-(biphenyl-4-yl)-2-bromo-7-phenyl-9,10-dihydroacridine (14 g, 28.6 mmol) was dissolved in toluene (500 mL) under a nitrogen atmosphere. Then, N-(biphenyl-4-yl)-N-(4-(4,4,5,5-tetramethyl-1,3,2-dioxaborolan-2-yl)phenyl)biphenyl-4-amine (15 g, 28.6 mmol) was added thereto. To the resultant mixture solution, tetrakis triphenyl phosphine palladium (1.32 g, 1.14 mmol) and potassium carbonate (9.9 g, 71.5 mmol) were added. Then, distilled water (70 mL) was added thereto, followed by reflux-stirring for 4 hours. The resultant solution was cooled to about 60° C., and purified by silica gel. Then, a toluene layer was extracted. The extracted organic solvent was concentrated and removed, and methanol was added to produce a solid. Through filtration, a yellowish brown solid was obtained. It was purified through silica gel column chromatography (methylene chloride/n-hexane (1/10)) to obtain N-(biphenyl-4-yl)-N-(4-(10-(biphenyl-4-yl)-7-phenyl-9,10-dihydroacridin-2-yl)phenyl)biphenyl-4-amine as a Cpd 14 compound (15 g, yield 65%, pale yellow solid).

$^1$H NMR: 3.8 (s, 2H), 6.4 (d, 2H), 6.6 (t, 8H), 7.0 (d, 2H), 7.3 (d, 2H), 7.6 (m, 20H), 7.9 (t, 8H).

Elemental Analysis for $C_{61}H_{44}N_2$: calcd C, 91.01; H, 5.51; N, 3.48. found C, 91.11; H, 5.46; N, 3.43. HRMS for $C_{61}H_{44}N_2$ [M]$^+$: calcd 804.35. found 804.35

Synthesis Example 2

Synthesis of Cpd 3 Compound

A Cpd 3 compound was synthesized as a pale yellow solid in the same manner as that in Synthesis Example 1.

Elemental Analysis for $C_{55}H_{40}N_2$: calcd C, 90.63; H, 5.53; N, 3.84. found C, 90.42; H, 5.77; N, 3.81. HRMS for $C_{55}H_{40}N_2$ [M]$^+$: calcd 728. found 728.

Synthesis Example 3

Synthesis of Cpd 36 Compound

A Cpd 36 compound was synthesized as a pale yellow solid in the same manner as that in Synthesis Example 1.

Elemental Analysis for $C_{47}H_{34}N_2$: calcd C, 90.06; H, 5.47; N, 4.47. found C, 90.47; H, 5.34; N, 4.19. HRMS for $C_{47}H_{34}N_2$ [M]$^+$: calcd 626. found 626.

Synthesis Example 4

Synthesis of Cpd 48 Compound

A Cpd 48 compound was synthesized as a pale yellow solid in the same manner as that in Synthesis Example 1.

Elemental Analysis for $C_{57}H_{40}N_2$: calcd C, 90.92; H, 5.35; N, 3.72. found C, 90.65; H, 5.40; N, 3.95. HRMS for $C_{57}H_{40}N_2$ [M]$^+$: calcd 752. found 752.

Synthesis Example 5

Synthesis of Cpd 61 Compound

A Cpd 61 compound was synthesized as a pale yellow solid in the same manner as that in Synthesis Example 1.

Elemental Analysis for $C_{47}H_{34}N_2$: calcd C, 90.06; H, 5.47; N, 4.47. found C, 89.86; H, 5.38; N, 4.76. HRMS for $C_{47}H_{34}N_2$ [M]$^+$: calcd 626. found 626.

Synthesis Example 6

Synthesis of Cpd 81 Compound

A Cpd 81 compound was synthesized as a pale yellow solid in the same manner as that in Synthesis Example 1.

Elemental Analysis for $C_{37}H_{26}N_2$: calcd C, 89.13; H, 5.26; N, 5.62. found C, 89.42; H, 5.33; N, 5.25. HRMS for $C_{37}H_{26}N_2$ [M]$^+$: calcd 498. found 498.

Synthesis Example 7

Synthesis of Cpd 102 Compound

A Cpd 102 compound was synthesized as a pale yellow solid in the same manner as that in Synthesis Example 1.

Elemental Analysis for $C_{53}H_{36}N_2$: calcd C, 90.83; H, 5.18; N, 4.00. found C, 90.91; H, 5.18, 3.91. HRMS for $C_{53}H_{36}N_2$ [M]$^+$: calcd 701. found 700.

Synthesis Example 8

Synthesis of Cpd 106 Compound

A Cpd 106 compound was synthesized as a pale yellow solid in the same manner as that in Synthesis Example 1.

Elemental Analysis for $C_{53}H_{36}N_2$: calcd C, 90.83; H, 5.18; N, 4.00. found C, 90.91; H, 5.18, 3.91. HRMS for $C_{53}H_{36}N_2$ $[M]^+$: calcd 701. found 700.

Synthesis Example 9

Synthesis of Cpd 113 Compound

A Cpd 113 compound was synthesized as a pale yellow solid in the same manner as that in Synthesis Example 1.

Elemental Analysis for $C_{49}H_{34}N_2$: calcd C, 90.43; H, 5.27; N, 4.30. found C, 90.66; H, 5.32; N, 4.02. HRMS for $C_{49}H_{34}N_2$ $[M]^+$: calcd 650. found 650.

Synthesis Example 10

Synthesis of Cpd 129 Compound

A Cpd 129 compound was synthesized as a pale yellow solid in the same manner as that in Synthesis Example 1.

Elemental Analysis for $C_{51}H_{42}N_2$: calcd C, 89.96; H, 5.92; N, 4.11. found C, 90.09; H, 5.95; N, 3.96. HRMS for $C_{51}H_{42}N_2$ $[M]^+$: calcd 681. found 680.

Synthesis Example 11

Synthesis of Cpd 131 Compound

A Cpd 131 compound was synthesized as a pale yellow solid in the same manner as that in Synthesis Example 1.

Elemental Analysis for $C_{57}H_{44}N_2$: calcd C, 90.44; H, 5.86; N, 3.70. found C, 90.58; H, 5.91; N, 3.51. HRMS for $C_{57}H_{44}N_2$ $[M]^+$: calcd 757. found 756.

Example 1

Fabrication of an Organic Electro-Luminescence Device

The compound synthesized in each of Synthesis Examples 1 to 11 was sublimation-purified with high purity, and then was used to fabricate a green organic electro-luminescence device according to the following steps.

On the ITO (anode), DS-205 (Doosan) was vacuum-deposited to a thickness of 800 Å so as to form a hole injection layer, and the Cpd 3 compound synthesized in Synthesis Example 2 was vacuum-deposited to a thickness of 150 Å on the hole injection layer to form a hole transport layer.

On the hole transport layer, the compound of Formula 2 as a host material, doped with 5% of the compound of Formula 3 as a dopant material, was vacuum-deposited to a thickness of 300 Å so as to form a light emitting layer. On the light emitting layer, Alq3 as an electron transport material was vacuum-deposited to a thickness of 250 Å so as to form an electron transport layer. On the electron transport layer, LiF as an electron injection material was deposited to a thickness of 10 Å to form an electron injection layer, and then on the electron injection layer, aluminum was vacuum-deposited to a thickness of 2000 Å to form a cathode.

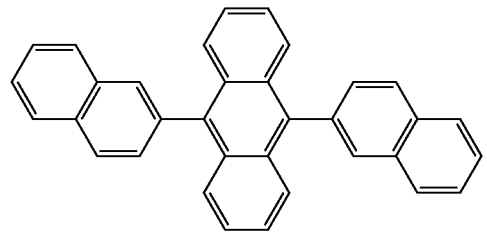

[Formula 2]

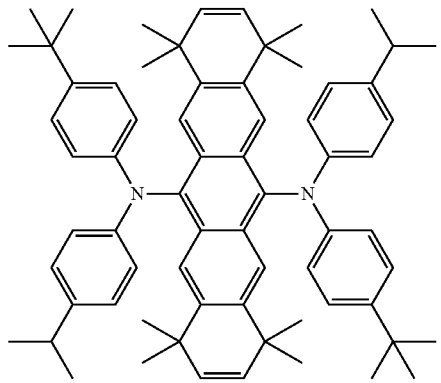

[Formula 3]

Example 2-11

Fabrication of an Organic Electro-Luminescence Device

An organic electro-luminescence device was fabricated in the same manner as described in Example 1 except that each of Cpd 14, Cpd 36, Cpd 48, Cpd 61, Cpd 81, Cpd 102, Cpd 106, Cpd 113, Cpd 129 and Cpd 131, instead of the Cpd 3 compound, was used in the formation of a hole transport layer.

Comparative Example 1

Fabrication of an Organic Electro-Luminescence Device

An organic electro-luminescence device was fabricated in the same manner as described in Example 1 except that α-NPB instead of the Cpd 3 compound was used in the formation of a hole transport layer.

Experimental Example

On each of organic electro-luminescence devices fabricated from Examples 1-11 and Comparative Example 1, the luminous efficiency was measured at a current density of 10 mA/cm², and the results are noted in Table 1 below.

TABLE 1

| | Hole transport layer | Operating voltage (V) | luminous efficiency (cd/A) |
|---|---|---|---|
| Example 1 | Cpd 3 | 5.5 | 23 |
| Example 2 | Cpd 14 | 5.4 | 24 |
| Example 3 | Cpd 36 | 5.8 | 22 |
| Example 4 | Cpd 48 | 6.2 | 22 |

TABLE 1-continued

| | Hole transport layer | Operating voltage (V) | luminous efficiency (cd/A) |
|---|---|---|---|
| Example 5 | Cpd 61 | 6.5 | 21 |
| Example 6 | Cpd 81 | 6.9 | 17 |
| Example 7 | Cpd 102 | 6.2 | 23 |
| Example 8 | Cpd 106 | 6.4 | 18 |
| Example 9 | Cpd 113 | 6.0 | 20 |
| Example 10 | Cpd 129 | 5.5 | 23 |
| Example 11 | Cpd 131 | 5.4 | 24 |
| Comparative Example | α-NPB | 5.8 | 13 |

All of the organic electro-luminescence devices from Examples 1-11 showed high luminance, and Example 2 (Cpd 14) and Example 11 (Cpd 131) showed similar levels (a low operating voltage, a high luminance, and a color purity level (x, y: 0.27, 0.63).

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A compound represented by Formula 1 below:

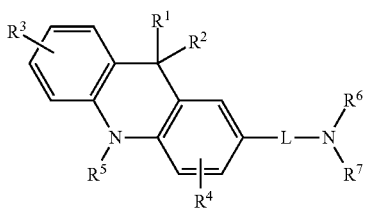

[Formula 1]

wherein, $R^1$ to $R^4$ are the same or different, and are selected from the group consisting of hydrogen, deuterium, halogen, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, a fused or non-fused $C_5$-$C_{60}$ heteroaryl group, a straight-chain or branched $C_1$-$C_{40}$ alkyloxy group, a fused or non-fused $C_6$-$C_{60}$ aryloxy group, and a fused or non-fused $C_6$-$C_{60}$ arylamine group;

$R^5$ to $R^7$ are the same or different, and are selected from the group consisting of hydrogen, deuterium, a straight-chain or branched $C_1$-$C_{40}$ alkyl group, a $C_3$-$C_{40}$ cycloalkyl group, a $C_3$-$C_{40}$ heterocycloalkyl group, a fused or non-fused $C_6$-$C_{60}$ aryl group, and a fused or non-fused $C_5$-$C_{60}$ heteroaryl group, and forms or does not form a ring fused to an adjacent group; and L represents a $C_6$-$C_{60}$ arylene group or a $C_5$-$C_{60}$ heteroarylene group.

2. The compound as claimed in claim 1, wherein L is a $C_6$-$C_{60}$ arylene group or a $C_5$-$C_{60}$ heteroarylene group, selected from the group consisting of phenylene, biphenylene, terphenylene, naphthylene, anthracenylene, phenanthrylene, pyrenylene, fluorenylene, fluoranthenylene, perylenylene, carbazolylene, N-carbazolephenylene, pyridinylene, quinolinylene and isoquinolinylene.

3. The compound as claimed in claim 1, wherein $R^1$ to $R^7$ and L each is independently substituted or unsubstituted with at least one substituent selected from the group consisting of deuterium, halogen, a nitrile group, a nitro group, a $C_1$-$C_{40}$ alkyl group, a $C_3$-$C_{40}$ cycloalkyl group, a $C_3$-$C_{40}$ heterocycloalkyl group, a $C_6$-$C_{60}$ aryl group, a $C_5$-$C_{60}$ heteroaryl group, a $C_1$-$C_{40}$ alkyloxy group, a $C_6$-$C_{60}$ aryloxy group and a $C_6$-$C_{60}$ arylamine group.

4. An organic electro-luminescence device comprising (i) an anode; (ii) a cathode; and (iii) one or more organic material layers intervened between the anode and the cathode, wherein at least one layer of the organic material layers comprises the compound represented by Formula 1 as claimed in claim 1.

5. The organic electro-luminescence device as claimed in claim 4, wherein the organic material layer comprising the compound represented by Formula 1 comprises one or more selected from the group including a hole injection layer, a hole transport layer, and a light emitting layer.

6. The organic electro-luminescence device as claimed in claim 4, wherein L comprises a $C_6$-$C_{60}$ arylene group or a $C_5$-$C_{60}$ heteroarylene group, selected from the group consisting of phenylene, biphenylene, terphenylene, naphthylene, anthracenylene, phenanthrylene, pyrenylene, fluorenylene, fluoranthenylene, perylenylene, carbazolylene, N-carbazolephenylene, pyridinylene, quinolinylene and isoquinolinylene.

7. The organic electro-luminescence device as claimed in claim 4, wherein $R^1$ to $R^7$ and L each is independently substituted or unsubstituted with at least one substituent selected from the group consisting of deuterium, halogen, a nitrile group, a nitro group, a $C_1$-$C_{40}$ alkyl group, a $C_3$-$C_{40}$ cycloalkyl group, a $C_3$-$C_{40}$ heterocycloalkyl group, a $C_6$-$C_{60}$ aryl group, a $C_5$-$C_{60}$ heteroaryl group, a $C_1$-$C_{40}$ alkyloxy group, a $C_6$-$C_{60}$ aryloxy group and a $C_6$-$C_{60}$ arylamine group.

* * * * *